(12) United States Patent
Borchert

(10) Patent No.: US 9,909,115 B2
(45) Date of Patent: Mar. 6, 2018

(54) HEAT-STABLE PERSEPHONELLA CARBONIC ANHYDRASES AND THEIR USE

(71) Applicant: Novozymes A/S, Bagsvaerd (DK)

(72) Inventor: Martin Simon Borchert, Hilleroed (DK)

(73) Assignee: Novozymes A/S, Bagsværd (DK)

( * ) Notice: Subject to any disclaimer, the term of this patent is extended or adjusted under 35 U.S.C. 154(b) by 343 days.

(21) Appl. No.: 14/639,685

(22) Filed: Mar. 5, 2015

(65) Prior Publication Data

US 2015/0175997 A1 Jun. 25, 2015

Related U.S. Application Data

(62) Division of application No. 13/818,519, filed as application No. PCT/EP2011/064585 on Aug. 24, 2011, now abandoned.

(60) Provisional application No. 61/376,898, filed on Aug. 25, 2010, provisional application No. 61/420,204, filed on Dec. 6, 2010.

(30) Foreign Application Priority Data

Aug. 24, 2010 (EP) .................................... 10173848
Dec. 1, 2010 (EP) .................................... 10193303

(51) Int. Cl.
*C12N 9/88* (2006.01)
*C12M 1/40* (2006.01)
*C12M 3/00* (2006.01)

(52) U.S. Cl.
CPC .............. *C12N 9/88* (2013.01); *C12M 21/18* (2013.01); *C12M 23/44* (2013.01); *C12Y 402/01001* (2013.01)

(58) Field of Classification Search
None
See application file for complete search history.

(56) References Cited

U.S. PATENT DOCUMENTS

| | | | |
|---|---|---|---|
| 6,143,556 A | 11/2000 | Trachtenberg | |
| 6,524,842 B1 | 2/2003 | Vainberg | |
| 7,132,090 B2 | 11/2006 | Dziedzic | |
| 2004/0029257 A1 | 2/2004 | Dutil | |
| 2005/0214936 A1 | 9/2005 | Bhattacharya | |

FOREIGN PATENT DOCUMENTS

| | | | |
|---|---|---|---|
| WO | 2004/007058 A1 | 1/2004 | |
| WO | 2004/028667 A1 | 4/2004 | |
| WO | 2004/104160 A1 | 12/2004 | |
| WO | 2005/114417 A2 | 12/2005 | |
| WO | 2006/089423 A1 | 8/2006 | |
| WO | 2008/095057 A2 | 8/2008 | |
| WO | WO 2008095057 A2 * | 8/2008 | ............ B01D 53/84 |
| WO | 2010/081007 A2 | 7/2010 | |

OTHER PUBLICATIONS

Reysenbach et al. Journal of Bacteriology. vol. 191, No. 6, p. 1992-1993 (2009).*
Reysenbach et al. Uniprot Accession No. C0QRB5 (2009).*
Peng et al., Journal of Peking University (Health Sciences), vol. 39, No. 2, pp. 210-212 (2007).
Gotz et al., International Journal of Systematic and Evolutionary Microbiology, vol. 52, pp. 1349-1359 (2002).
Kohl et al., Gas Purification, fifth edition, Part 1, pp. 1187-1237 (1997).
Kohl et al., Gas Purification, fifth edition, Part 2, pp. 40-115 (1997).
Kohl et al., Gas Purification, fifth edition, Part 3, pp. 116-186 (1997).
Kohl et al., Gas Purification, fifth edition, Part 4, pp. 330-377 (1997).
Kohl et al, Gas Purification, fifth edition, Part 5, pp. 378-414 (1997).
Reysenbach et al., GenBank Accession No. YP_002731211.1 (2009).
Reysenbach et al., Journal of Bacteriology, vol. 191, No. 6, pp. 1992-1993 (2009).
Reysenbach et al., UniProt Accession No. C0QRB5 (2009).

* cited by examiner

*Primary Examiner* — Paul J Holland
(74) *Attorney, Agent, or Firm* — Eric J. Fechter

(57) ABSTRACT

The present invention relates to use of *Persephonella* carbonic anhydrase in $CO_2$ extraction, e.g., from flue gas, natural gas, biogas or ambient air. The *Persephonella* carbonic anhydrases are especially well suited for these purpose due to their extreme thermostability.

18 Claims, 3 Drawing Sheets

HEAT-STABLE PERSEPHONELLA CARBONIC ANHYDRASES AND THEIR USE

CROSS-REFERENCE TO RELATED APPLICATIONS

This application is a divisional of U.S. application Ser. No. 13/818,519 filed on Feb. 22, 2013, now abandoned, which is a 35 U.S.C. 371 national application of PCT/EP11/64585 filed Aug. 24, 2011, which claims priority or the benefit under 35 U.S.C. 119 of European application nos. 10173848.2 and 10193303.4 filed Aug. 24, 2010 and Dec. 1, 2010, respectively, and U.S. provisional application Nos. 61/376,898 and 61/420,204 filed Aug. 25, 2010 and Dec. 6, 2010, respectively. The content of each application is fully incorporated herein by reference.

REFERENCE TO A SEQUENCE LISTING

This application contains a Sequence Listing in computer readable form, which is incorporated herein by reference.

FIELD OF THE INVENTION

The present invention relates to use of carbonic anhydrases obtainable from *Persephonella marina* in $CO_2$ extraction, e.g., from flue gasses, biogas, natural gas or ambient air. The invention also relates to bioreactors for extracting carbon dioxide and compositions useful for such extraction processes.

BACKGROUND OF THE INVENTION

Carbon dioxide ($CO_2$) emissions are a major contributor to the phenomenon of global warming. $CO_2$ is a by-product of combustion and it creates operational, economic, and environmental problems. $CO_2$ emissions may be controlled by capturing $CO_2$ gas before emitted into the atmosphere. There are several chemical approaches to control the $CO_2$ emissions (A. Kohl and R. Nielsen, Gas Purification, 5$^{th}$ ed., Gulf Professional Publishing, Houston, Tex., 1997). However, many of these approaches have drawbacks such as high energy consumption, slow processes, and use of ecologically questionable or toxic compounds.

An enzyme based approach using the capability of carbonic anhydrase to catalyse the conversion of $CO_2$ to bicarbonate at a very high rate (turnover is up to $10^5$ molecules of $CO_2$ per second), overcomes the reaction rates and environmental issues in relation to $CO_2$ capture. Technical solutions for extracting $CO_2$ from gases, such as combustion gases or respiration gases, using carbonic anhydrases have been described in WO 2006/089423, U.S. Pat. No. 6,524,842, WO 2004/007058, WO 2004/028667, US 2004/0029257, U.S. Pat. No. 7,132,090, WO 2005/114417, U.S. Pat. No. 6,143,556, WO 2004/104160, US 2005/0214936, WO 2008/095057. Generally, these techniques operate by bringing a soluble or immobilized carbonic anhydrase into contact with $CO_2$ which either may be in a gas phase or a liquid phase. In the presence of water, carbonic anhydrase catalyses the conversion of $CO_2$ into bicarbonate ions which may be further protonated or deprotonated to carbonic acid and/or carbonate ions depending on the pH of the medium. The ions may either be utilized to facilitate growth of algae or microorganisms that utilize bicarbonate/carbonate as a carbon source, to induce a pH change in a surrounding medium or supply buffering capacity, to provide bicarbonate/carbonate as an active agent for subsequent chemical processes, or precipitated as a carbonate salt, or converted back into pure $CO_2$, which can then be used (for example in enhanced oil recovery, for production of urea, for food and beverage processing, or to supply $CO_2$ to greenhouses or cultivation ponds), released (for example from a contained life support environment such as a submarine, spacecraft, or artificial lung), compressed (for example for transportation through pipelines), or stored (such as in geological or deep oceanic formations or saline aquifers).

Mammalian, plant and prokaryotic carbonic anhydrases (alpha- and beta-class CAs) generally function at physiological temperatures (37° C.) or lower temperatures. The temperature of combustion gasses or the liquids into which they are dissolved may, however, easily exceed the temperature optimum for the carbonic anhydrase used to capture the $CO_2$. One of the drawbacks of using enzyme based solutions is that extensive cooling may be needed in $CO_2$ extraction processes prior to contacting the $CO_2$-containing gas/liquid with the carbonic anhydrase, and cooling is an energy consuming process. Consequently, there is a need for more heat-stable carbonic anhydrases when the enzyme is to be used under industrially relevant conditions.

Figure 1:
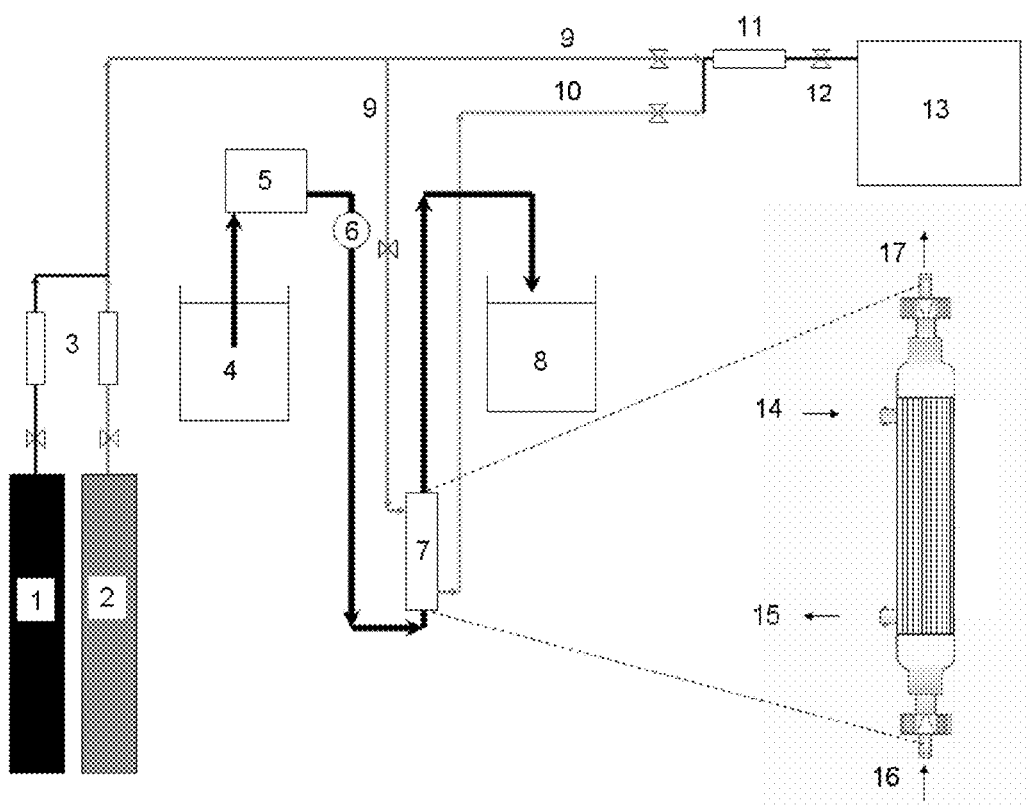
FIG. 1 is a schematic presentation of a hollow fiber membrane bioreactor. The numbers represent the following features: 1. Carbon Dioxide ($CO_2$) tank; 2. Nitrogen ($N_2$) tank; 3. Mass flow controllers (MFC); 4. Carrier liquid reservoir; 5. Liquid pump; 6. Pressure gauge; 7. Hollow fiber membrane module; 8. Waste; 9. Feed gas; 10. Scrubbed gas; 11. Mass flow meter (MFM); 12. Gas sampling valve; 13. Gas chromatograph; 14. Feed gas in; 15. Scrubbed gas out; 16. Liquid in; 17. Liquid out.

is the *Bacillus subtilis* pectate lyase gene locus used for homologous recombination into the host cell genome. "Neo" is the kanamycin resistance gene. "Amp" is the beta-lactamase gene. "cryIIIA region" is the triple promoter system including the cryIIIA stabilizing element.

SUMMARY OF THE INVENTION

One aspect of the present invention is the use of carbonic anhydrases derived from or producible by bacteria of the genus *Persephonella*, for extraction of carbon dioxide from a carbon dioxide-containing medium. The carbonic anhydrases used in the present invention maintain a least 30%, preferably at least 40%, more preferably at least 50% residual activity after 15 minutes, preferably 2 hours in 1 M $NaHCO_3$ buffer pH 8.0 at temperatures at or above 55° C., preferably at or above 60° C., preferably at or above 65° C., more preferably at or above 70° C., 75° C., 80° C., or 85° C., even more preferably at or above 90° C. and most preferably above 100° C. The heat-stable carbonic anhydrases are in particular used in a bioreactor capable of extracting $CO_2$ emitted from combustion, or from raw natural gas or a syngas or a biogas or ambient air when conditions in the extraction process require the enzyme to be exposed to high temperatures. The enzymes may, however, also be employed in processes which do not occur at elevated temperatures, since they also maintain activity at lower temperatures, e.g., 0° C., room temperature (20 to 25° C.) and 37° C. The heat stability is also useful when exposing carbonic anhydrase to high temperature environments (i.e., where the temperature can exceed 45° C., 50° C. or even 55° C.) during manufacture, use, or during idle periods, for example storage in a hot warehouse. Heat stability during use may include situations where carbonic anhydrase carries out useful catalysis at one temperature (e.g., 45° C., 50° C., 55° C., 60° C. or 65° C.) and then, due to different stage(s) in the process of use, is exposed to higher temperatures (e.g., 70° C., 75° C., 80° C., 85° C., 90° C., 95° C. or 100° C.) where it either also carries out useful catalysis, or remains idle until exposed to a next stage of the process, such as at a lower temperature, where carbonic anhydrase again carries out useful catalysis. In these situations, carbonic anhydrase may have to withstand repeated exposure to lower and higher temperatures during the process of use, hence a heat stable carbonic anhydrase is needed.

In a further aspect, the invention provides a composition comprising a matrix suitable for immobilization and a carbonic anhydrase derived from or producible by bacteria of the genus *Persephonella*.

In a further aspect, the present invention provides a bioreactor suitable for extracting carbon dioxide.

DETAILED DESCRIPTION OF THE INVENTION

One aspect of the present invention concerns the use of a carbonic anhydrase obtainable from or producible by bacteria strains of the genus *Persephonella* for the extraction of $CO_2$ from $CO_2$-containing media, such as a gas, a liquid or multiphase mixture. The present invention is in particular useful where the temperature of the $CO_2$-containing medium is above the temperature optimum for commercially available carbonic anhydrases, such as CA-I or CA-II isolated from human or bovine erythrocytes.

Definitions

The term "carbonic anhydrase activity" or "CA activity" is defined herein as an EC 4.2.1.1 activity which catalyzes the conversion between carbon dioxide and bicarbonate $[CO_2+H_2O \leftrightarrows HCO_3^-+H^+]$. For purposes of the present invention, CA activity is determined according to the procedure described in Example 4. One unit of CA activity is defined after Wilbur [1 $U=(1/t_c)-(1/t_u) \times 1000$] where U is units and $t_c$ and $t_u$ represent the time in seconds for the catalyzed and uncatalyzed reaction, respectively (Wilbur, 1948, *J. Biol. Chem.* 176: 147-154). The polypeptides of the present invention are considered to have CA activity if they have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the CA activity of the polypeptide consisting of the amino acid sequence corresponding to amino acid residues 20 to 243 of SEQ ID NO: 2 or amino acid residues 29 to 251 of SEQ ID NO: 4.

The terms "$CO_2$-lean" and "$CO_2$-rich" carrier liquid are terms used in the present invention to describe the relative amount of carbon (e.g., in the form of dissolved $CO_2$, chemically reacted $CO_2$, bicarbonate, carbonic acid and/or carbonate salt) present in the carrier liquid as it circulates through the process. As used herein, the term "$CO_2$-lean carrier liquid" generally refers to carrier liquid entering an absorption module. The term "$CO_2$-rich carrier liquid" generally refers to a carrier liquid entering a desorption module. It is understood that the term "$CO_2$-lean carrier liquid" can also be applied to carrier liquid exiting a desorption module, and the term "$CO_2$-rich carrier liquid" can also be applied to carrier liquid exiting an absorption module. $CO_2$-rich carrier liquid contains more carbon compared to $CO_2$-lean carrier liquid within a system at a given point in time.

The term "$CO_2$-containing medium" is used to describe any material which contains at least 0.001% $CO_2$, preferably at least 0.01%, more preferably at least 0.1%, more preferably at least 1%, more preferably at least 5%, most preferably 10%, even more preferred at least 20%, and even most preferably at least 50% $CO_2$. Preferably the $CO_2$-containing medium has a temperature between 5° C. and 110° C., more preferably between 10° C. and 100° C., more preferably between 20° C. and 95° C., more preferably between 30° C. and 90° C., more preferably between 40° C. and 85° C., more preferably between 50° C. and 80° C., more preferably between 55° C. and 75° C. and most preferably between 60° C. and 70° C. at any pressure. $CO_2$-containing media are in particular gaseous phases (including gas mixtures), liquids or multiphase mixtures, but may also be solid. A $CO_2$-containing gaseous phase is for example raw natural gas obtainable from oil wells, gas wells, and condensate wells, syngas generated by the gasification of a carbon containing fuel (e.g., methane) to a gaseous product comprising CO and $H_2$, or emission streams from combustion processes, e.g., from carbon based electric generation power plants, or from flue gas stacks from such plants, industrial furnaces, stoves, ovens, or fireplaces or from airplane or car exhausts. A $CO_2$-containing gaseous phase may alternatively be ambient air (including hot (above 40° C.) air, e.g., desert air), or from respiratory processes in mammals (such as the $CO_2$-containing gas phase in an artificial lung), living plants and other $CO_2$ emitting species, in particular from green-houses. A $CO_2$-containing gas phase may also be off-gas, from aerobic or anaerobic fermentation, such as brewing, fermentation to produce useful products such as ethanol, or the production of biogas. Such fermentation processes can occur at elevated temperatures if they are facilitated by thermophilic microorganisms, which are for example encountered in the production of biogas. A $CO_2$-containing gaseous phase may alternatively be a gaseous phase enriched in $CO_2$ for the purpose of use or storage. The above described gaseous phases may also occur as multiphase mixtures, where the gas co-exists with a certain degree of fluids (e.g., water or other solvents) and/or solid materials (e.g., ash or other particles). $CO_2$-containing liquids are any solution or fluid, in particular aqueous liquids, containing measurable amounts of $CO_2$, preferably at one of the levels mentioned above at any pressure. $CO_2$-containing liquids may be obtained by passing a $CO_2$-containing gas or solid (e.g., dry ice or soluble carbonate containing salt) into the liquid. $CO_2$-containing fluids may also be compressed $CO_2$ liquid (that contains contaminants, such as dry-cleaning fluid), supercritical $CO_2$, or $CO_2$ solvent liquids, like ionic liquids. A $CO_2$-containing liquid may also be referred to as a "carrier liquid". A $CO_2$-containing liquid may also include compounds capable of improving the $CO_2$-containing capacity of the liquid, such as $HCO_3$ ($KHCO_3$ or $NaHCO_3$), $CO_3^{2-}$ ($Na_2CO_3$ or $K_2CO_3$), $HPO_4^{2-}$ ($K_2HPO_4$ or $Na_2HPO_4$) or MDEA or Tris.

The term "$CO_2$ extraction" is to be understood as a reduction of carbon from a $CO_2$-containing medium. Such an extraction may be performed from one medium to another, e.g., gas to liquid, liquid to gas, gas to liquid to gas, liquid to liquid or liquid to solid, but the extraction may also be the conversion of $CO_2$ to bicarbonate, carbonate or carbonic acid within the same medium or the conversion of bicarbonate to $CO_2$ within the same medium. The term $CO_2$ capture is also used to indicate extraction of $CO_2$ from one medium to another or conversion of $CO_2$ to bicarbonate/carbonate or conversion of bicarbonate/carbonate to $CO_2$.

When used herein the term "coding sequence" means a polynucleotide sequence, which directly specifies the amino acid sequence of product polypeptide. The boundaries of the coding sequence are generally determined by an open reading frame, which usually begins with the ATG start codon or alternative start codons such as GTG and TTG and ends with a stop codon such as TAA, TAG and TGA. The coding sequence may be a DNA, cDNA, mRNA, synthetic or recombinant polynucleotide.

The term "functional fragment of a polypeptide" or "a polypeptide fragment having carbonic anhydrase activity" is used to describe a polypeptide which is derived from a longer polypeptide (parent polypeptide), e.g., a mature polypeptide, and which has been truncated either in the N-terminal region or the C-terminal region or in both regions to generate a fragment of the parent polypeptide. To be a functional polypeptide the fragment must maintain at least 20%, preferably at least 40%, more preferably at least 50%, more preferably at least 60%, more preferably at least 70%, more preferably at least 80%, even more preferably at least 90%, most preferably at least 95%, and even most preferably at least 100% of the CA activity of the parent polypeptide.

The term "identity" is used to describe the relatedness between two amino acid sequences or two nucleic acid sequences. For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Alignment−Total Number of Gaps in Alignment)

The term "heat-stable" or "thermostable" as used in reference to an enzyme, such as a carbonic anhydrase, indicates that the enzyme is functional or active (i.e., can perform catalysis) at an elevated temperature, i.e., above 45° C., preferably above 50° C., more preferably above 55° C., more preferably above 60° C., even more preferably above 65° C., most preferably above 70° C., most preferably above 75° C., most preferably above 80° C., most preferably above 85° C. most preferably above 90° C., and even most preferably above 100° C. In a preferred embodiment the carbonic anhydrase displays optimum activity at one of the temperatures indicated above, i.e., the enzyme's temperature optimum is at one of the temperatures indicated above. The temperature stability of the carbonic anhydrase can be increased to some extent by way of formulation, e.g., by combination with stabilizing chemicals or by immobilization of the enzyme or by chemical modification, e.g., cross-linking, to preserve the enzyme in its active three dimensional shape. In order for an enzyme to be considered as heat-stable it remains active after at least 15 minutes, preferably for at least 2 hours, more preferably for at least 24 hours, more preferably for at least 7 days, more preferably for at least 10 days, even more preferably for at least 14 days, most preferably for at least 30 days, even most preferably for at least 50 days at the elevated temperature. Generally, the level of activity is measured using the assay described in Example 3 after incubation for the given time in 1 M $NaHCO_3$ buffer at pH 8 at the given elevated temperature. The activity may be compared with the enzyme activity prior to the temperature elevation, thereby obtaining the residual activity of the enzyme after the heat treatment. Preferably, the residual activity is at least 30% after the given time at the elevated temperature, more preferably at least 40%, more preferably at least 50%, more at least 60%, even more preferably at least 70%, most preferably at least 80%, even most preferably the residual activity is at least 90%, and absolutely most preferred the level of residual activity is at least equal to or unchanged after the given time at the elevated temperature.

The term "host cell" means any cell type that is susceptible to transformation, transfection, transduction, and the like with a nucleic acid construct or expression vector comprising a polynucleotide of the present invention. The term "host cell" encompasses any progeny of a parent cell that is not identical to the parent cell due to mutations that occur during replication.

The term "isolated polynucleotide" means a polynucleotide that is modified by the hand of man relative to that polynucleotide as found in nature. In one aspect, the isolated polynucleotide is at least 1% pure, e.g., at least 5% pure, more at least 10% pure, at least 20% pure, at least 40% pure, at least 60% pure, at least 80% pure, at least 90% pure, and at least 95% pure, as determined by agarose electrophoresis. The polynucleotides may be of genomic, cDNA, RNA, semisynthetic, synthetic origin, or any combinations thereof.

The term "isolated polypeptide" as used herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE.

The term "mature polypeptide" means a polypeptide in its final form following translation and any post-translational modifications, such as N-terminal processing, C-terminal truncation, glycosylation, phosphorylation, etc. In one aspect, the mature polypeptide is 20 to 243 of SEQ ID NO: 2 or amino acid residues 29 to 251 of SEQ ID NO: 4. It is known in the art that a host cell may produce a mixture of two of more different mature polypeptides (i.e., with a different C-terminal and/or N-terminal amino acid) expressed by the same polynucleotide).

The term "mature polypeptide coding sequence" means a polynucleotide that encodes a mature polypeptide having carbonic anhydrase activity.

The term "operably linked" means a configuration in which a control sequence is placed at an appropriate position relative to the coding sequence of a polynucleotide such that the control sequence directs the expression of the coding sequence.

The term "secreted polypeptide" as used herein is to be understood as a polypeptide which after expression in a cell is either transported to and released to the surrounding extracellular medium or is associated/embedded in the cellular membrane so that at least a part of the polypeptide is exposed to the surrounding extracellular medium.

The term "subsequence" means a polynucleotide having one or more (several) nucleotides deleted from the 5' and/or 3' end of a mature polypeptide coding sequence, wherein the subsequence encodes a fragment having carbonic anhydrase activity.

The term "substantially pure polypeptide" denotes herein a polypeptide preparation which contains at most 10%, preferably at most 8%, more preferably at most 6%, more preferably at most 5%, more preferably at most 4%, at most 3%, even more preferably at most 2%, most preferably at most 1%, and even most preferably at most 0.5% by weight of other polypeptide material with which it is natively associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation. The polypeptides of the present invention are preferably in a substantially pure form. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods.

Herein, the term "substantially pure polypeptide" is synonymous with the terms "isolated polypeptide" and "polypeptide in isolated form".

The term "syngas" or "synthesis gas" is used to describe a gas mixture that contains varying amounts of carbon monoxide and hydrogen generated by the gasification of a carbon containing fuel (e.g., methane or natural gas) to a gaseous product with a heating value. $CO_2$ is produced in the syngas reaction and must be removed to increase the heating value.

The term "thermophilic" in relation to an organism, describes an organism which thrives at relatively high temperatures, i.e., above 45° C. Hyperthermophilic organisms thrive in extremely hot environments, that is, hotter than around 60° C. with an optimal temperature above 80° C.

Carbonic Anhydrases Obtainable from *Persephonella* and their Use

Currently, a few heat-stable carbonic anhydrases are known, including the beta-class CA (Cab) from *Methanobacterium thermoautotrophicum* ΔH, which has been reported to be heat stable to up to 75° C. (Smith and Ferry, 1999, *J. Bacteriol.* 181: 6247-6253) and the gamma-class carbonic anhydrase (Cam) from *Methanosarcina thermophila* TM-1. Cam was isolated for the first time in 1994 (Alber and Ferry, 1994, *Proc. Natl. Acad. Sci. USA* 91: 6909-1913), and in 1996 it was shown to be stable to heating at 55° C. for 15 min (Alber and Ferry, 1996, *J. Bacteriol.* 178: 3270-3274). Cam is the only isolated enzyme of the gamma-class, and has been subject to a lot of characterization studies since its discovery. WO 2010/081007 describes heat stable variants of Cam. US 2006/0257990 describes variants of human carbonic anhydrase II where the most stable variant shows activity up to 65° C. US 2004/0259231 discloses the use of Cab as well as the non-thermostable human CA isoform IV in a $CO_2$ solubilization and concentration process. WO 2008/095057 describes heat-stable alpha-carbonic anhydrases from *Bacillus clausii* and *Bacillus halodurans* and their use for the extraction of $CO_2$. WO 2010/151787 (application no. PCT/US2010/040022) describes heat-stable alpha-carbonic anhydrases from *Caminibacter* and their use for the extraction of $CO_2$.

One aspect of the present invention is the technical application of heat-stable carbonic anhydrases isolated from bacteria strains of the genus *Persephonella*, or carbonic anhydrases which fall within the given sequence identity of the *Persephonella* carbonic anhydrases of the invention, in the extraction of $CO_2$ from a $CO_2$-containing medium, such as a gas, a liquid, or multiphase mixture. Preferably, the *Persephonella* carbonic anhydrase is an alpha-class carbonic anhydrase. Preferably, the $CO_2$ is extracted from one medium, such as a gas, to a second medium such as a liquid involving the conversion of $CO_2$ to bicarbonate within the second medium, this is also termed absorption of $CO_2$. The reverse extraction process where bicarbonate in the $CO_2$-containing medium is converted to $CO_2$ which can then be released from the first medium to a second medium, such as a gas, is also a desirable process where the carbonic anhydrase of the present invention can be applied. This process is also termed desorption of $CO_2$. The present invention is in particular useful where the temperature of the $CO_2$-containing medium and/or the temperature of certain stages of the extraction process where carbonic anhydrase is present is above the temperature optimum for commercially available carbonic anhydrases, such as CA-I or CA-II isolated from human or bovine erythrocytes, which have temperature optimums at approximately 37° C., or where the temperature is above the temperature optimum of the few known thermostable carbonic anhydrases. One example of a process stage where elevated temperatures may occur is when the hot flue gas is brought into contact with the carbonic anhydrase containing liquid used to absorb the $CO_2$ from the flue gas. Another example is the current $CO_2$ scrubbing technologies, such as chemical absorption with carbonates (e.g., hot potassium carbonate process), alkanolamines (e.g., monoethanolamine, methyldiethanolamine, etc.) or other amines (e.g., ammonia), which use elevated temperatures (up to about 120 to 130° C.) in the desorption process.

Several bacterial strains belonging to the genus *Persephonella* have been isolated from deep-sea hydrothermal vents. Currently, three species have been identified, namely *Persephonella marina*, *Persephonella hydrogeniphila* and *Persephonella guaymasensis* (Götz, et al., 2002, *International Journal of Systematic and Evolutionary Microbiology*, 52, 1349-1359 and Nakagawa, et al., 2003, *International Journal of Systematic and Evolutionary Microbiology*, 53, 863-869). The strains have been reported to grow at temperatures at or around 70° C. *Persephonella marina* has been subjected to genomic sequencing (EMBL-EBI ID CP001230). The open reading frame identified as SEQ ID NO: 1 in the present application was obtained from this work, and it was predicted that the translated polypeptide sequence published with UniProt accession nr. C0QRB5 (SEQ ID NO: 2) may give rise to a protein with carbonic anhydrase activity. It appears that the protein has never been expressed or characterized to confirm this prediction. The examples of the present invention describe, for the first time, the cloning, expression and isolation of the mature carbonic anhydrase from *P. marina* DSM 14350 and confirm that the amino acid sequence gives rise to an enzyme with carbonic anhydrase activity. It was shown that the enzyme maintained all its carbonic anhydrase activity after incubation in 1 M $NaHCO_3$ at pH 8 at 80° C. for 15 minutes as well as for 2 hours.

The carbonic anhydrase which is most closely related to the *Persephonella* carbonic anhydrase with UniProt accession nr: C0QRB5, is *Allochromatium vinosum* carbonate dehydratase (EC 4.2.1.1, UNIPROT accession nr: D3RV11) which is 53% identical.

In one embodiment of the present invention the carbonic anhydrase to be applied in the extraction of $CO_2$ is derived from, obtainable from or producible by bacteria strains selected from one of the species *Persephonella marina*, *Persephonella hydrogeniphila* or *Persephonella guaymasensis*, preferably the carbonic anhydrase to be applied in the extraction of $CO_2$ is derived from or producible by one of the strains deposited as *Persephonella marina* DSM 14350, *Persephonella hydrogeniphila* DSM 15103 or *Persephonella guaymasensis* DSM 14351.

In a further embodiment the carbonic anhydrases to be applied in the extraction of $CO_2$ is a) derived from, obtainable from or producible by *Persephonella marina* DSM 14350; or b) a polypeptide having an amino acid sequence corresponding to amino acid residues 20 to 243 of SEQ ID NO: 2 or amino acid residues 29 to 251 of SEQ ID NO: 4; or c) a polypeptide which is at least 60%, 65%, 70%, 75%, 80%, 85%, 90%, 91%, 92%, 93%, 94%, 95%, 96%, 97%, 98% or 99% identical to amino acid residues 20 to 243 of SEQ ID NO: 2 or amino acid residues 29 to 251 of SEQ ID NO: 4; or d) a fragment of (a) or (b) or (c) having carbonic anhydrase activity; or e) a polypeptide encoded by a nucleic acid sequence which hybridizes under very low, low, medium, medium-high or high stringency conditions with: i) a polynucleotide sequence encoding a mature polypeptide of SEQ ID NO: 2; or ii) a polynucleotide sequence of SEQ ID NO: 1 or SEQ ID NO: 3; or iii) a subsequence of (i) or (ii), of at least 100 contiguous nucleotides, or iv) a complementary strand of (i) or (ii) (Sambrook, Fritsch, and Maniatis, 1989, *Molecular Cloning, A Laboratory Manual*, 2d edition, Cold Spring Harbor, N.Y.); or f) a polypeptide encoded by a nucleic acid sequence which, because of the degeneracy of the genetic code, does not hybridize with the polynucleotide sequence of SEQ ID NO: 1 or SEQ ID NO: 3, but which codes for a polypeptide having an amino acid sequence according to b) or c); or g) a polypeptide encoded by a nucleic acid sequence which is at least 60%, 65%, 70%, 75%, 80%, 85%, 90%, 91%, 92%, 93%, 94%, 95%, 96%, 97%, 98%, 99% or 100% identical to SEQ ID NO: 1 or SEQ ID NO: 3. The polypeptide in c), e) or g) can be synthetic or derived from other species than *Persephonella* as long as the polypeptide fall within the claimed identities and maintain carbonic anhydrase activity. When the term *Persephonella* carbonic anhydrase is used it also includes the carbonic anhydrases of c), e) and g).

In accordance with the present invention hybridization conditions are defined as follows. For long probes of at least 100 nucleotides in length, very low to very high stringency conditions are defined as prehybridization and hybridization at 42° C. in 5×SSPE, 0.3% SDS, 200 micro-g/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency). In a particular embodiment, the wash is conducted using 0.2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency). In another particular embodiment, the wash is conducted using 0.1×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency). For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures. The carrier material is washed once in 6×SCC plus 0.1% SDS for 15 minutes and twice each for 15 minutes using 6×SSC at 5° C. to 10° C. below the calculated $T_m$.

Polypeptide sequences with a given % identity to SEQ ID NO: 2 or SEQ ID NO: 4 or polynucleotide sequences with a given % identity to SEQ ID NO: 1 or SEQ ID NO: 3, may be obtained from naturally occurring sources such as other bacterial strains. Alternatively, the polypeptide or polynucleotide sequences may be obtained by substitution, deletion, and/or insertion of one or more amino acids or nucleic acids in the parent sequence (for example the mature sequences of SEQ ID NO: 1 or SEQ ID NO: 3 for polynucleotides and SEQ ID NO: 2 or SEQ ID NO: 4 for polypeptides). Preferably the number of amino acids which is changed in the parent sequence or the polypeptide encoded by the parent polynucleotide is between 1 to 5, 1 to 10, 1 to 20, 1 to 30 or 1 to 40 amino acids. The amino acid changes are, preferably, of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a polyhistidine tag or a polyhistidine-glutamine tag, an antigenic epitope or a binding domain. Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by Neurath and Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly. In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Essential amino acids in the parent polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for biological activity (i.e., carbonic anhydrase activity) to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. A large number of these analyses have already been performed on carbonic anhydrases, the most important are for example reviewed in Tripp et al., 2001, J. Biol. Chem. 276: 48615-48618 and Lindskog, 1997, Pharmacol. Ther. 74: 1-20. The identities of essential amino acids can also be inferred from analysis of identities with polypeptides which are related to a polypeptide according to the invention.

Alpha-carbonic anhydrases are identified by their consensus sequence motif: S-E-[HN]-x-[LIVM]-x(4)-[FYH]-x(2)-E-[LIVMGA]-H-[LIVMFA](2). The respective consensus residues corresponds to positions 112 to 128 in SEQ ID NO: 2 and in positions 120 to 136 in SEQ ID NO: 4. In a preferred embodiment all consensus positions are present in the carbonic anhydrase.

The following amino acid residues H107, H109, and H126 (numbering according to SEQ ID NO: 2) are predicted to form a histidine triad which is important for catalysis. In a preferred embodiment of the present invention the carbonic anhydrase contains a histidine in position, 107, 109, and 126 (using SEQ ID NO: 2 numbering).

The following amino acid residues H82, E113, Q105 and T193 (using SEQ ID NO: 2 numbering) are predicted to participate in a proton shuttle mechanism, which also is relevant for the catalytic activity of the enzyme (analogous to Human CAII as described by Smith and Ferry, 2000, FEMS Microbiol Rev. 24: 335-366.). In a further embodiment the carbonic anhydrase contains a histidine in position 82 (using SEQ ID NO: 2 numbering) and/or a glutamine in position 105 (using SEQ ID NO: 2 numbering) and/or a glutamic acid in position 113 (using SEQ ID NO: 2 numbering) and/or a threonine in position 193 (using SEQ ID NO: 2 numbering). Preferably, at least one of the proton shuttle positions are present, more preferably at least two proton shuttle positions are present, more preferably at least three proton shuttle positions are present and most preferably all the proton shuttle positions are present in the carbonic anhydrase.

The following cysteine residues C44 and 0197 (using SEQ ID NO: 2 numbering) are predicted to engage in a cysteine bridge and may therefore be important for the stability of the carbonic anhydrase. Respective cysteine residues were previously identified in Neisseria gonorrhoeae CA (Huang et. al., 1998, J Mol Biol, 283: 301-310.). In a preferred embodiment of the present invention the carbonic anhydrase contains a cysteine in position 44 and 197 (using SEQ ID NO: 2 numbering).

Single or multiple amino acid substitutions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochem. 30:10832-10837; U.S. Pat. No. 5,223,409; WO 92/06204), and region-directed mutagenesis (Derbyshire et al., 1986, Gene 46:145; Ner et al., 1988, DNA 7:127).

Mutagenesis/shuffling methods can be combined with high-throughput, automated screening methods to detect activity of cloned, mutagenized polypeptides expressed by host cells. Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The *Persephonella* carbonic anhydrases described above are useful in a series of applications which are described in more detail below. When referring to *Persephonella* carbonic anhydrase or carbonic anhydrase below it is intended to include all the carbonic anhydrases described in the present invention in particular if they fall within the claimed identities.

In particular *Persephonella* carbonic anhydrase may be used for carbon dioxide extraction from $CO_2$ emission streams, e.g., from carbon-based or hydrocarbon-based combustion in electric generation power plants, or from flue gas stacks from such plants, industrial furnaces, stoves, ovens, or fireplaces or from airplane or car exhausts. *Persephonella* carbonic anhydrases may also be used to remove $CO_2$ in the preparation of industrial gases such as acetylene ($C_2H_2$), carbon monoxide (CO), chlorine ($Cl_2$), hydrogen ($H_2$), methane ($CH_4$), nitrous oxide ($N_2O$), propane ($C_3H_8$), sulfur dioxide ($SO_2$), argon (Ar), nitrogen ($N_2$), and oxygen ($O_2$). *Persephonella* carbonic anhydrase can also be used to remove $CO_2$ from a raw natural gas during the processing to natural gas. Removal of $CO_2$ from the raw natural gas will serve to enrich the methane ($CH_4$) content in the natural gas, thereby increasing the thermal units/m³. Raw natural gas is generally obtained from oil wells, gas wells, and condensate wells. Natural gas contains between 1% to 10% $CO_2$ when obtained from geological natural gas reservoirs by conventional methods, but depending on the natural source or recovery method used may contain up to 50% $CO_2$ or even higher. Carbonic anhydrase can also be used to purify the natural gas such that it is substantially free of $CO_2$, e.g., such that the $CO_2$ content is below 1%, preferably below 0.5%, 0.2%, 0.1%, 0.05% and most preferably below 0.02%. In resemblance to the methane enrichment of natural gases, carbonic anhydrases can also be used to enrich the methane content in biogases. Biogases will always contain a considerable degree of $CO_2$, since the bacteria used in the fermentation process produce methane (60-70%) and $CO_2$ (30-40%). Biogas production may be performed using mesophilic or thermophilic microorganisms. Thermophilic strains allow the fermentation to occur at elevated temperatures, e.g., from 40° C. to 80° C., or from 50° C. to 70° C., or from 55° C. to 60° C. In such processes a heat-stable carbonic anhydrase is particularly useful to remove $CO_2$ from the methane. The present invention provides for the use of a *Persephonella* carbonic anhydrase to reduce the carbon dioxide content in a biogas, preferably the $CO_2$ content is reduced such that it constitutes less than 25%, more preferably less than 20%, 15%, 10%, 5%, 2%, 1%, 0.5% and most preferably less than 0.1%. In a preferred embodiment the carbonic anhydrase is heat-stable. Furthermore, carbonic anhydrase may be applied in the production of syngas by removing the $CO_2$ generated by the gasification of a carbon containing fuel (e.g., methane or natural gas) thereby enriching the CO, $H_2$ content of the syngas. Where syngas production occurs at elevated temperatures the use of a heat-stable carbonic anhydrase is an advantage. The present invention provides for the use of a carbonic anhydrase to reduce the carbon dioxide content in a syngas production. Preferably, the $CO_2$ content is reduced such that it constitutes less than 25%, more preferably less than 20%, 15%, 10%, 5%, 2%, 1%, 0.5% and most preferably less than 0.1%. In a preferred embodiment the carbonic anhydrase is heat-stable. Preferably, the carbonic anhydrases to be used for $CO_2$ extraction as described above maintain residual activity of at least 30%, preferably above 40%, more preferably above 50%, more preferably above 60%, even more preferably above 70%, most preferably above 80%, most preferably above 85%, most preferably above 90%, most preferably above 95%, and even most preferably the residual activity is unchanged after incubation in 1 M $NaHCO_3$ buffer pH 8 at temperatures above 45° C., preferably above 50° C., above 55° C., above 60° C., above 65° C., more preferably above 70° C., most preferably above 80° C., most preferably above 90° C., most preferably above 100° C., most preferably above 105° C. and even most preferably above 110° C. for at least 15 minutes, preferably for at least 2 hours, more preferably for at least 24 hours, more preferably for at least 7 days, more preferably for at least 10 days, even more preferably for at least 14 days, most preferably for at least 30 days, even most preferably for at least 50 days at the elevated temperature. The temperature stability and/or longevity of the carbonic anhydrase can be increased to some extent by formulation, e.g., by immobilization of the enzyme.

In a particular embodiment, the carbonic anhydrase of the invention, which may be used for $CO_2$ extraction as described above, maintains at least 85% activity when incubated for 15 minutes in 1 M $NaHCO_3$ solution (approximately pH 8-10) in the temperature range 25-90° C. At 50° C., the enzyme maintains full activity over the pH range 4-11 for one day. After 10 days at 50° C., the enzyme maintains more than 50% activity over the pH range 4-11.

In an aspect of the present invention the $CO_2$ extraction from a $CO_2$-containing medium is performed in enzyme based bioreactors. Before the carbon dioxide-containing medium is processed in a bioreactor, it may be purified to free it from contaminants which may disturb the enzymatic reaction or interfere with bioreactor functionality in other ways, e.g., by clotting outlets or membranes. Gasses/multiphase mixtures emitted from combustion processes, e.g., flue gases or exhausts, are preferably cleared of ash, particles, $NO_x$ and/or $SO_2$, before the gas/multiphase mixture is passed into the bioreactor. The raw natural gas from different regions may have different compositions and separation requirements. Preferably, oil, condensate, water and natural gas liquids, if present in the raw natural gas, are removed prior to the extraction of $CO_2$ in an enzyme based bioreactor. The $CO_2$ emitted from combustion processes or present in the raw natural gas may be extracted in the same process as the sulfur removal, or it may be extracted in a completely separate process. If the gas at this point exceeds the temperature optimum of the carbonic anhydrase of the present invention, some degree of cooling may be needed. The temperature to which carbonic anhydrase is exposed during $CO_2$ extraction process whether it is the process temperature in the bioreactor or the feed gas temperature may be between 0° C. and 120° C. Preferably the process temperature is between 45° C. and 110° C., more preferably between 50° C. and 100° C., more preferably between 55° C. and 90° C. even more preferably between 60° C. and 80° C., and most preferably between 65° C. and 75° C.

Reactors and processes for gas separation, including $CO_2$ extraction, are well known in the art and are used commercially for various purposes (A. Kohl and R. Nielsen, Gas Purification, 5$^{th}$ ed., Gulf Professional Publishing, Houston, Tex., 1997). There are several types of reactors which may be combined with the carbonic anhydrase of the present invention to generate a bioreactor (a reactor comprising biological material such as an enzyme) for extracting $CO_2$ from gases, such as combustion gases or respiration gases. Because carbonic anhydrase improves the rate of $CO_2$ extraction, combining carbonic anhydrase with the $CO_2$ extraction reactor enables reactor and process improvements such as smaller size and less expensive absorption modules (e.g., shorter absorption column) and use of low energy consuming and low volatility carrier liquids, as well as overall lower operating temperatures compared to the conventional approaches.

One type of reactor uses liquid membranes. This may for example be reactors including hollow fiber membranes containing a liquid film as described in Majumdar et al., 1988, *AIChE* 34: 1135-1145; U.S. Pat. No. 4,750,918; U.S. Pat. No. 6,156,096; WO 04/104160. Such hollow fiber membrane-based designs are also sometimes termed hollow fiber liquid membranes (HFLM) and the $CO_2$ separation devices based on these have been termed hollow fiber contained liquid membrane (HFCLM) permeators. A common feature of HFCLM permeators is that the hollow fibers enclosing the feed and sweep gas streams are near (i.e., "tightly packed" or "immediately adjacent") to one another and they are enclosed in a single rigid treatment chamber to form one complete permeator. In such a design, a liquid surrounds the shell side of the tightly packed feed and sweep hollow fibers. Because the distance between the outside wall of one hollow fiber is very close to adjacent hollow fibers the thickness of the liquid layer between them is thin, like a membrane, and the composition of the liquid only allows certain components to pass, hence the term "liquid membrane" has been used to describe the liquid surrounding the hollow fibers. Contained liquid membrane permeators where the liquid film is sandwiched between two structural support membranes have also been described in the art (Cowan et al., 2003, *Ann. NY Acad. Sci.* 984: 453-469); this design essentially functions in the same way as the HFCLM. Contained liquid membrane permeators have also been used in combination with carbonic anhydrase as described in U.S. Pat. No. 6,143,556, WO 2004/104160, Cowan et al., 2003, *Ann. NY Acad. Sci.* 984: 453-469; and Trachtenberg et al., 2003, SAE international Conference on Environmental Systems Docket number 2003-01-2499. In these cases, the $CO_2$ desorption step takes place in the same enclosed treatment chamber as the absorption step. Another example describes an amine based $CO_2$ capture reactor based on absorber/desorber hollow fiber membrane modules (Kosaraju et al., 2005, *Ind. Eng. Chem. Res.* 44:1250-1258).

Another type of reactor uses direct gas-liquid contact. This may for example be conventional solvent based $CO_2$ capture reactors that are based on absorber/desorber column reactors (US 2008/0056972, Reddy et al., *Second National Conference on Carbon Sequestration, NETL/DOE*, Alexandria, Va., May 5-8, 2003). Example flow schemes for commercial direct gas-liquid contactor reactors that use alkanolamines (such as monoethanolamine, diethanolamine, and methyldiethanolamine) for $CO_2$ extraction are shown in A. Kohl and R. Nielsen, Gas Purification, $5^{th}$ ed., a Gulf Professional Publishing, Houston, Tex., 1997: 57-62. Example flow schemes for commercial direct gas-liquid contactor reactors that use alkaline salt solutions (such as potassium carbonate) for $CO_2$ extraction are shown in A. Kohl and R. Nielsen, Gas Purification, $5^{th}$ ed., Gulf Professional Publishing, Houston, Tex., 1997: 334-340. Direct gas-liquid contact reactors using carbonic anhydrase have been described in U.S. Pat. No. 6,524,843; WO 2004/007058, WO 2004/056455, U.S. Pat. No. 7,176,017, and US 2004/0059231. In this type of reactor the gas phase or multiphase mixture, is contacted with a liquid phase under conditions where the $CO_2$ in the gas phase is absorbed by the liquid phase where it is converted into bicarbonate by carbonic anhydrase. The bicarbonate enriched liquid is removed from the reactor by a continuous flow, to ensure that the equilibrium between $CO_2$ and bicarbonate is shifted towards continuous conversion of $CO_2$. The gas phase dissolution into the liquid phase is dependent on the surface contact area between the gas and liquid. A large contact area can for example be achieved by passing liquid and $CO_2$-containing gas through a high surface area packed, tray or plate column or tower, by spraying small droplets of liquid through the $CO_2$-containing gas (i.e., a spray contactor), or by bubbling the $CO_2$-containing gas through the liquid (i.e., bubble tank or pond), or by a combination of these techniques. Packed columns can comprise packings such as raschig rings, berl saddles, lessing rings, intalox metal, intalox saddles, pall rings or engineered packings such as Q-PAC (Lantec Products, Inc., Agoura Hills, Calif. 91301). The packing materials may be comprised of a polymer such as nylon, polyester, polyethylene, polyetheretherketone, polypropylene, polystyrene or fluoropolymer (e.g., polytetrafluoroethylene), a ceramic such as silica, or a metal such as aluminium, carbon steel, or stainless steel, or a cellulose-based material such as wood or cotton fiber. In reactor types where the liquid is continuously exchanged or when it is desirable to restrain carbonic anhydrase to one or more locations in the reactor, carbonic anhydrase may be retained in the reactor by various means. In the packed columns the carbonic anhydrase can be immobilized on the packing material (for methods of immobilizing CA, see for example in WO 2005/114417). In the "bubbling" reactors the carbonic anhydrase can be entrapped in a porous substrate, for example, an insoluble gel particle such as silica, alginate, alginate/chitosan, alginate/carboxymethylcellulose, or the carbonic anhydrase can be immobilized (by covalent bonds, ionic charges, entrapment or encapsulation) on a solid packing (as in the packed columns) in suspension in the liquid, or the carbonic anhydrase can be chemically linked in an albumin or PEG network. Carbonic anhydrase can also be restrained to a particular location in the reactor by entrapment in a polymeric immobilization material which may comprise a micellar or inverted micellar material, such as described in WO 2010/037109. Spray contactors may include vertical or horizontal spray chambers, countercurrent spray columns, venturi scrubbers, ejectors or jet $5^{th}$ scrubbers, cyclone scrubbers, and spray dryers (A. Kohl and R. Nielsen, Gas Purification, ed., Gulf Professional Publishing, Houston, Tex., 1997: 418-427 and 604-616). Use of spray contactors is desirable when avoiding pressure drop and tolerance to solid particulates in the gas, such as with atmospheric pressure post-combustion exhaust gas is important. However, to be most effective, the rate of $CO_2$ absorption in spray contactors must be fast, and carbonic anhydrase can provide the needed catalysis to achieve these fast rates.

$CO_2$ extraction in a direct gas-liquid contact reactor may involve a first absorption stage followed by optionally a subsequent desorption, precipitation, utilization, collection, regeneration or release stage. A general description of the absorption stage is as follows. When the absorption reactor is in operation, a water-containing liquid enters the reactor at one end, preferably the top, and flows to the other end, preferably the bottom, and the $CO_2$-containing gas stream (feed gas) enters the reactor at one end, preferably at the opposite end (the bottom) ("countercurrent") from the liquid and the gas passes through the liquid and exits, minus the $CO_2$ extracted into the liquid, through a gas outlet at the opposite end (preferably, the top of the reactor). The liquid that exits the absorption reactor is enriched in bicarbonate/carbonate ($CO_2$-rich liquid) and the exit gas is reduced in the $CO_2$ content compared to the feed gas. The $CO_2$-rich liquid may be processed in subsequent reactions, for example to generate pure $CO_2$ by passing through a desorption reactor, or produce carbonate precipitates such as $CaCO_3$. The $CO_2$-rich liquid from the absorption reactor can also be utilized, e.g., to enhance algae growth, collected, e.g., by pumping the $CO_2$-rich liquid into a contained geological formation, released, e.g., by pumping the $CO_2$-rich liquid into the environment, such as release of bicarbonate liquid into seawater from a submarine life support system, evaporated or desalinated. The $CO_2$-rich liquid containing bicarbonate anion can be used in industrial processes, such as in the manufacturing processes for ammonium carbonate and ammonium bicarbonate, which are useful as fertilizer, or in processes for the removal and neutralization of acid gases such as sulfur dioxide.

The reactors described above may involve only an absorption stage, only a desorption stage or absorption followed by a desorption stage in which carbonic anhydrase may catalyze either the hydration of $CO_2$ to bicarbonate or the dehydration of bicarbonate to $CO_2$ or both. The reactors can be combined with each other where each reactor constitutes a module. For example can a liquid membrane reactor function as absorption module and the direct gas-liquid contact reactor function as a desorption module or vice versa.

Figure 2:
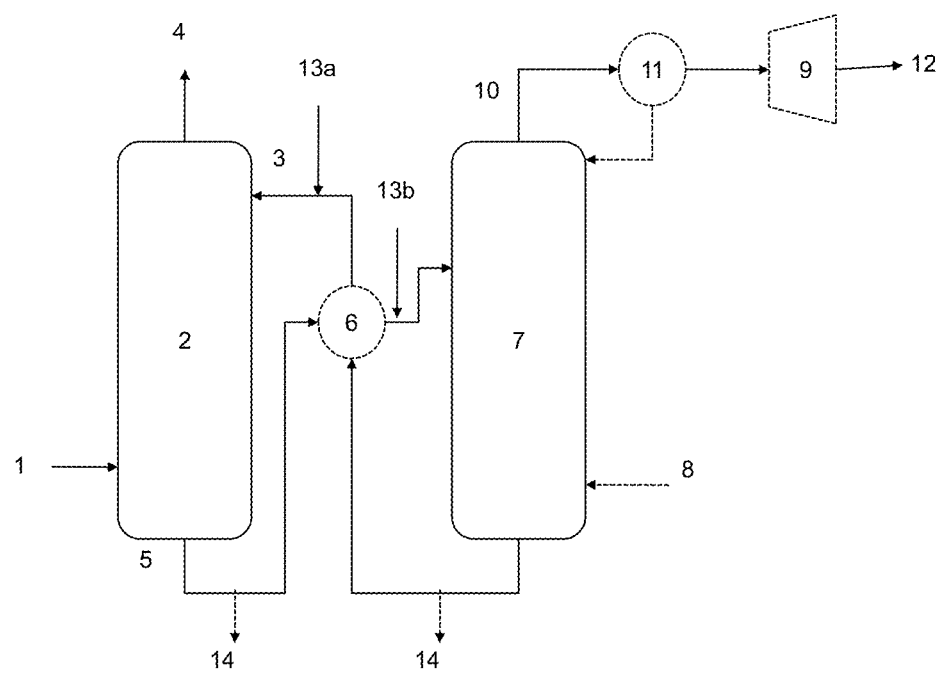
FIG. 2 is a schematic presentation of a general recirculating absorption/desorption process for $CO_2$ extraction from a mixed gas. In the general process, $CO_2$-rich Feed Gas (1) enters the Absorption Module (2) preferably the gas enters one end (e.g., the bottom) where it comes in contact with $CO_2$-Lean Carrier Liquid (3) entering the absorption module, preferably at the opposite end from the feed gas (e.g., the top). Scrubbed Gas (4), from which $CO_2$ has been removed, exits the absorption module. $CO_2$-Rich Carrier Liquid (5) exits the absorption module and (optionally) passes through a Temperature Regulator (e.g., a heat exchanger) (6) before entering (preferably at one end (e.g., the top)) the Desorption Module (7). Heat (8), such as supplied by a re-boiler or direct steam, or Vacuum (9), or a combination of these applied to the desorption module causes extracted $CO_2$ to be released from the carrier liquid and exit (10) the desorption module, (optionally) passing through a Condenser (11) to remove carrier liquid vapor prior to compression and/or use of the Purified $CO_2$ Gas (12). $CO_2$-Lean carrier liquid exits the desorption module and (optionally) passes through a temperature regulator (e.g., heat exchanger) before returning to the absorption module. Depleted and/or auxiliary carrier liquid components can be added at various points in the process, such as at the locations indicated (13a and 13b). Insoluble contaminants can be removed from the circulating liquid at various points in the process, such as at the locations indicated (14).

Without limiting the scope of the present invention, FIG. 2 is provided to illustrate a general schematic of a $CO_2$ extraction reactor comprising both absorption and desorption modules through which the $CO_2$ absorbing carrier liquid circulates as it removes $CO_2$ from a $CO_2$-containing gaseous phase (Feed Gas) in the absorber, releases Purified $CO_2$ Gas in the desorber, then recirculates back to the absorber. The term "Feed gas" is often used in relation to $CO_2$ extraction reactors where it implies that $CO_2$ is removed from the $CO_2$ containing gaseous phase by contact with a $CO_2$-lean carrier liquid in the reactor. The feed gas may be at atmospheric pressure, or at pressures above or below atmospheric pressure. Selective solubility of $CO_2$ in the carrier liquid causes extraction of $CO_2$ from the feed gas into the carrier liquid in the absorber. In the desorber, $CO_2$ is released from the carrier liquid by introducing a pressure difference (for example, a lower partial pressure of $CO_2$ in the desorber gas phase compared to that in the feed gas, such as can be achieved by applying vacuum in the desorber) that lowers the solubility of $CO_2$ in the carrier liquid and/or applying heat, e.g., via a reboiler, steam or a sweep gas to drive $CO_2$ into the gas phase in the desorber. Heat energy alone can be used to drive desorption such as is commonly used in monoethanol amine-based $CO_2$ extraction processes. For example the temperature in the desorber of a typical monoethanol amine-based $CO_2$ extraction is greater than 100° C. (e.g., 120° C.). Alternatively heat energy can be combined with pressure reduction to drive desorption in this case the temperature in the desorber can be lowered. For example, together with a reduced pressure (e.g., vacuum) compared to the pressure in the absorber (e.g., atmospheric pressure), the desorber can be operated at 70° C. A difference in pH can be used to facilitate absorption and desorption, wherein $CO_2$ absorption into an aqueous medium is favored at more alkaline pH whereas $CO_2$ desorption from an aqueous medium is favored at a less alkaline (more acidic) pH. The range of relevant pH difference ("swing") between absorption and desorption depends on the particular process. For example, for the sake of illustration, $CO_2$ absorption into a bicarbonate-based carrier liquid can occur at pH 9 or above resulting in a decrease in the pH of that carrier liquid to below pH 9. Desorption of $CO_2$ from that carrier liquid can then occur at pH below pH 9.

A pressure difference between the absorber and the desorber can be established/occur when the pressure of the feed gas passing through the absorber is higher than the pressure of the gas phase in the desorber. In some cases, such as for natural gas upgrading, the gas pressure in the absorber is higher than in the desorber and the gas pressures in both the absorber and the desorber may be above atmospheric pressure. In other cases, the gas pressure in the absorber is above atmospheric pressure and the gas pressure in the desorber is at or below atmospheric pressure (i.e., equal to or less than 100 kPa). Alternatively, a pressure difference between the absorber and the desorber can be established/occur when the pressure of the feed gas (such as a coal-fired post-combustion flue gas) passing through the absorber is approximately at atmospheric pressure and the pressure of the gas phase in the desorber is below atmospheric pressure. In one embodiment of the present invention, the total gas pressure difference between the absorber and the desorber is at least about 35 kPa.

The absorber and desorber shown schematically in FIG. 2 can be at essentially the same ("isothermal") temperature or at different temperatures. *Persephonella* carbonic anhydrase may be present in only the absorber or the desorber or both. Regeneration of $CO_2$ using vacuum (low pressure) at low temperatures, e.g., 70° C. in the desorber where a high temperature carbonic anhydrase such as *Persephonella* carbonic anhydrase is present is a further embodiment of the present invention. Carbonic anhydrase in such process catalyzes both absorption and desorption of $CO_2$ to and from absorption solvent. When the absorber and desorber are at different temperatures, a temperature regulator (e.g., heat exchanger) can be used to conserve energy in the process.

In a further illustration, a modification of the vacuum carbonate process for $H_2S$ absorption (A. Kohl and R. Nielsen, Gas Purification, 5$^{th}$ ed., a Gulf Professional Publishing, Houston, Tex., 1997: 383-388) has been described for $CO_2$ extraction (US 2007/0256559) and disclosed in combination with carbonic anhydrase (Lu et al., DOE Project No. DE-FC26-08NT0005498, NETL CO2 Capture Technology for Existing Plants R&D Meeting, Mar. 24-26, 2009, Pittsburgh, Pa.). In this illustration, atmospheric pressure power plant flue gas contacts aqueous potassium carbonate and carbonic anhydrase in the absorber column at temperatures in the range 40 to 60° C., where carbonic anhydrase is said to improve the rate of $CO_2$ hydration to bicarbonate in the carrier liquid. The $CO_2$-rich carrier liquid is pumped to a desorber column ("stripper") where $CO_2$ is released from the carrier liquid by a combination of low pressure (e.g., 14-55 KPa) and the application of heat (e.g., 50-70° C.) obtained by directly injecting low pressure, low quality exhaust steam from a low pressure steam turbine of the power plant. Carbonic anhydrase from *Persephonella* of the present invention is especially suitable for use in the described modified vacuum carbonate process because *Persephonella* carbonic anhydrase can tolerate temperatures both in the absorber and the desorber, meaning that, unlike other known carbonic anhydrases that would be inactivated by the temperature in the desorber, *Persephonella* carbonic anhydrase could tolerate the temperature in the desorber, allowing it to circulate along with the carrier liquid through both absorption and desorption stages of the process. The ability of *Persephonella* carbonic anhydrase to continuously circulate through the reactor along with the carrier liquid through regions of high and low temperature gives the added advantage that open spray tower/chamber reactor configurations can be used, which eliminates the need for packing materials. Physical agitation, including ultrasonic agitation, can be combined with vacuum and/or heat to enhance release of $CO_2$ from the carrier liquid in the desorber.

A further type of reactor uses membranes in combination with $CO_2$ hydration catalysis by carbonic anhydrase followed by precipitation. In one case, $CO_2$ is removed from a gaseous stream by passing the gaseous stream through a gas diffusion membrane into solution where conversion to is accelerated by passing the $CO_2$ solution over a matrix that contains carbonic anhydrase and adding a mineral ion to cause precipitation of the carbonic acid salt (U.S. Pat. No. 7,132,090). It has been shown further that carbonic anhydrase not only can catalyze the $CO_2$ hydration/dehydration reaction but also can promote the precipitation of calcium carbonate (Mirjafari et al., 2007, *Ind. Eng. Che. Res.*, 46: 921-926).

A further type of reactor removes $CO_2$ from ambient air. A reactor designed to remove $CO_2$ from ambient air have been reported (Stolaroff et al. 2008 *Environ. Sci. Technol.*, 42: 2728-2735), however this reactor does not utilize carbonic anhydrase. Without being bound by the design of the reported ambient air reactor, a carbonic anhydrase combined with suitable carrier liquids as disclosed in the present invention, could be used in such a reactor or in other reactor designs as described herein. A heat stable carbonic anhydrase is especially useful because exposure of the reactor to environmental conditions, such as sunlight, may increase the liquid temperature beyond the tolerance of known carbonic anhydrases, and avoids the need to cool the reactor. This illustrates a situation where the process of extracting $CO_2$ from the $CO_2$-containing medium may require carbonic anhydrase to function at or tolerate higher temperatures than the initial temperature of the $CO_2$-containing medium, such as ambient air, which may be cold at night (below 10° C.) and hot during the day (above 45° C.).

The different membrane reactors and direct gas-liquid contact reactors described above as well as other alternatives may be applied in a carbon dioxide extraction process, where the absorption process and desorption process occur in at least two steps. Such reactors generally comprise the following elements: a) at least one absorption module, which may comprise a gas inlet zone and/or a gas outlet zone; b) at least one desorption module comprising a gas outlet zone; c) a carrier liquid; and d) means for connecting the absorption module(s) and the desorption module(s) such that the carrier liquid can pass from the absorption module(s) to the desorption module(s). Optionally the means for connecting the absorption and desorption modules is a circuit, allowing the carrier liquid to be returned to the absorption module once it has passed through the desorption module. One or both of the modules may comprise at least one $CO_2$-permeable membrane which separates a gas phase from a liquid phase, such as described in WO 2010/014773 and WO 2010/014774. This module type is also termed a gas-liquid membrane (GLM) module. The GLM module may, e.g., be in the form of a hollow fiber membrane, a flat sheet membrane or a spiral-wound membrane. The GLM module may either function as an absorber module and/or a desorber module. Alternatively, one of the modules may be a GLM module and the other module may be composed such that the gas and liquid phases are in direct contact or in other words the gas-liquid interface is not separated by a membrane. This module type is also termed a direct gas-liquid contact (DGLC) module or just a direct contact (DC) module. The DGLC module may, e.g., be in the form of a column filled with packing material that allows for gas-liquid contact, and/or a liquid-containing vessel equipped with an inlet for exposing gas to the liquid (such as a bubble column), and/or a liquid-spray (such as a spray tower) and/or an aerator module and/or a falling film. The DGLC module may either function as an absorber module or a desorber module. Bubble cap system, sieve plate system, disk-and-doughnut column and packed column are examples of direct gas-liquid contact modules (DGLC).

The reactor types described above may be operated at any desired temperature. In one embodiment, the reactor is operated with a temperature of the liquid in contact with and/or containing carbonic anhydrase between 0° C. and 120° C. or 5° C. and 110° C., more preferably between 10° C. and 100° C., more preferably between 20° C. and 95° C., more preferably between 30° C. and 90° C., more preferably between 40° C. and 85° C., more preferably between 50° C. and 80° C., more preferably between 55° C. and 75° C., and most preferably between 60° C. and 70° C.

The absorption and desorption rates of $CO_2$ are dependent on the pH in the carrier liquid. In the reactor types described in relation to the present invention the pH of the $CO_2$-lean carrier liquid is between pH 4 to 12, preferably above pH 7 (as measured at room temperature, e.g., 20-25° C.), more preferably above pH 8, more preferably between 8 and 12, more preferably between 8 and 10.5, more preferably between 8.5 and 10, even more preferably between 9 and 9.5. Due to the hydration of $CO_2$ to carbonic acid (which immediately dissociates in water to bicarbonate) during absorption, the pH of the carrier liquid decreases as the carbon content of the $CO_2$-rich carrier liquid increases. The extent of pH decrease depends on the buffering capacity of the carrier liquid and the amount of $CO_2$ absorbed. In a preferred embodiment of the present invention the carrier liquid is a bicarbonate buffer, such as sodium bicarbonate, potassium bicarbonate, cesium bicarbonate, ammonium bicarbonate or another suitable salt of the bicarbonate where depending on the pH greater or lesser amount of carbonate and/or carbonic acid will exist together with bicarbonate.

In one embodiment of the present invention, the $CO_2$-rich carrier liquid passes through a desorption stage where the pH of the $CO_2$-rich carrier liquid will increase as the $CO_2$ is released. In order to recirculate carrier liquid through such an absorption-desorption system, it is preferred that the pH of the carrier liquid returns to the pH of the $CO_2$-lean carrier liquid before again passing through the absorption stage.

In a preferred embodiment of the present invention the reactor is equipped with means for regulating pH in the carrier liquid. This can be performed in several ways. One way is to add an alkaline substance to the carrier liquid, e.g., at one of the auxiliary components addition points (13*a*) indicated in FIG. 2, using automatic pH adjustment equipment such as an automatic titrator. The alkaline substance preferably has a similar composition (e.g., concentration of solvent, ionic strength, amount of carbonic anhydrase, etc.) as the carrier liquid circulating in the system and can be added at any time before absorption for adjustment of pH.

Similarly a neutral to acidic substance can be added to the carrier liquid any time before desorption, e.g., at one of the auxiliary components addition points (13*b*) indicated in FIG. 2. Extra carrier liquid can be removed from the system if needed, e.g., at one of the removal points (14) indicated in FIG. 2.

In the $CO_2$ capture processes described above the *Persephonella* carbonic anhydrase of the present invention may be combined with one or more other carbonic anhydrases. The different process steps in the whole $CO_2$ capture process may require different operating conditions, e.g., temperature, pH, carrier liquid compositions, pressure and so forth. The carbonic anhydrases of the present invention may be combined with other carbonic anhydrases operating at different optimal conditions which are needed in the $CO_2$ capture process. For example, one carbonic anhydrase could circulate in the carrier liquid and a different carbonic anhydrase could be immobilized at one or more locations in the reactor.

The carbonic anhydrase of the present invention or enzyme based bioreactors described above comprising a carbonic anhydrase of the present invention, also find more unconventional applications such as in pilot cockpits, submarine vessels, aquatic gear, safety and firefighting gear and astronaut's space suits and artificial lung devices to keep breathing air free of toxic $CO_2$ levels. Other applications are to remove $CO_2$ from confined spaces, such as to reduce hazardous $CO_2$ levels from inside breweries and enclosed buildings carrying out fermentation, and from $CO_2$ sensitive environments like museums and libraries, to prevent excessive $CO_2$ from causing acid damage to books and artwork. A further alternative application is to remove $CO_2$ from hot ambient air, e.g., in a desert. In this case the carbonic anhydrase could for example be comprised in a reactor suitable for extracting $CO_2$ from ambient air as described in Stolaroff et al., 2008, *Environ. Sci. Technol.* 42: 2728-2735, such a reactor could for example take the form of an "artificial tree" or a windmill as described in WO 2008/041920.

*Persephonella* carbonic anhydrase can be used as an independent $CO_2$ extraction catalyst or it may alternatively be combined with conventional $CO_2$ extraction technologies such as chemical absorption via amine-based solvents or aqueous ammonia or physical solvents such as Selexol™ (Union Carbide) or polyethylene glycol ethers. In a further embodiment of the present invention a *Persephonella* carbonic anhydrase is combined with a carbon dioxide absorbing compound such as amine-based compounds for example aqueous alkanolamines including monoethanolamine (MEA), diethanolamine (DEA), methyldiethanolamine (MDEA), 2-amino-2-hydroxymethyl-1,3-propanediol (Tris), diglycolamine (DGA), 2-amino-2-methyl-1-propanol (AMP), 2-amino-2-hydroxymethyl-1,3-propanediol (AHPD), diisopropanol amine (DIPA), aqueous soluble salts (e.g., sodium or potassium salts) of N-methylaminopropionic acid or N,N-dimethylaminoacetic acid or N-methylalanine, N-methylglycine, beta-alanine (3-aminopropanoic acid) or other natural or modified amino acids (e.g., N-substituted amino acid derivatives), 2-(2-aminoethylamino) ethanol (AEE), triethanolamine (TEA) or other primary, secondary, tertiary or hindered amine-based solvents including those described on pages 7 to 9 of U.S. Pat. No. 4,112,052 (hereby incorporated by reference), or aqueous soluble salts of glycine (e.g., sodium or potassium glycinate) and taurine or other liquid absorbers such as aqueous NaOH, KOH, LiOH, carbonate salt (e.g., sodium, potassium, or ammonium) or bicarbonate salt solutions at different ionic strengths, molar concentrations (ranging from dilute solutions to highly concentrated solutions, up to the solubility limit of the salts, which may vary based on the temperature) or aqueous electrolyte solutions and promoters such as piperazine, or polyethylene glycol ethers, or a blend of them or analogs or blends thereof. The aqueous soluble salts and solvents may be combined with pH buffering and mineral sequestering compounds, such as phosphate salts, polyphosphate salts and borate salts, to provide mixed salt solutions, such as potassium bicarbonate with potassium phosphate. The aqueous soluble salts and solvents may be combined with simple electrolytes (e.g., alkali halides, such as NaCl, KCl, and metal halides, such as $ZnCl$). The combination may either be applied in the bioreactors described above or it may be applied to already existing $CO_2$ scrubbing facilities based on conventional techniques. In conventional bioreactors, the concentration of alkanolamines is typically 15-30 weight percent. In an embodiment of the present invention the concentration of alkanolamines could be in the conventional range or preferably at a lower concentration such as preferably below 15% (V/V), more preferably below 12%, 10%, 8%, 6%, 5%, 4%, 3%, 2%, 1%, 0.5%, 0.2% and most preferably below 0.1% (V/V).

In conventional processes, corrosion and oxidation inhibitors, such as contained in Fluor Daniel's proprietary Econ-Amine FG solvent, are added to provide for increasing the amine concentration while reducing the risk of corrosion. Inorganic corrosion inhibitors include vanadium (e.g., sodium metavanadate), antimony, copper, cobalt, tin, and sufur compounds. Organic corrosion inhibitors include thiourea and salicylic acid.

Other auxiliary carrier liquid components can include wetting agents, chelating agents (e.g., ethylenediamine tetraacetic acid, polyphosphate salts), and viscosity reducers, and other compounds capable of increasing the flux of $CO_2$ into or out of the carrier liquid.

In conventional processes, techniques to reduce and/or avoid foam formation are commonly employed. These include removal of foam-causing impurities prior to $CO_2$ extraction and use of antifoaming agents and foam inhibitors such as silicone compounds or high-boiling alcohols such as oleyl alcohol or octylphenoxyethanol (A. Kohl and R. Nielsen, Gas Purification, $5^{th}$ ed., Gulf Professional Publishing, Houston, Tex., 1997: 224-230).

Another aspect of the present invention relates to biogas production where the $CO_2$ extraction is performed directly in the biogas fermentation broth, as an alternative to passing the biogas through a bioreactor as described above. By adding *Persephonella* carbonic anhydrase to the anaerobic broth, more $CO_2$ from the gas phase can be converted into bicarbonate, which is the substrate for methane production by the methanogenic Archaea. Particularly, the genus *Methanosarcina* is frequently present in thermophilic biogas digesters (Mladenovska and Ahring, 2000, *FEMS Microbiol. Ecol.* 3: 225-229). It has been shown for *Methanosarcina thermophila* ™-1 that bicarbonate may be a limiting factor for the methane production, for example cultures of *M. thermophila*™-1 grown in low bicarbonate solution (0.6 mM) showed a considerable lag phase (i.e., methane production began later) when compared with cultures containing ten times higher bicarbonate dosages (6 mM). Additionally, the total yield of methane was 25 times less at the lower bicarbonate dosage (Murray and Zinder, 1985, *Appl. Environ. Microbiol.* 50: 49-55). Consequently, a heat-stable carbonic anhydrase will be particularly useful if the biogas production is performed at elevated temperatures using one or more thermophilic microorganisms, for example methanogens like *Methanosarcina* sp. that can use $CO_2$/bicarbonate as carbon source for growth and methanogenesis.

A further embodiment of the present invention is use of a *Persephonella* carbonic anhydrase of the present invention as an additive in a biogas fermentation broth.

A further embodiment of the present invention is use of a *Persephonella* carbonic anhydrase to enhance growth of algae and other aquatic plants that utilize bicarbonate as a carbon source by catalyzing the conversion of $CO_2$ to bicarbonate in or for delivery to the aquatic plant environment. This approach can, for example, be used to simultaneously remove $CO_2$ from a combustion exhaust gas, such as a flue gas, and provide $CO_2$ for conversion to bicarbonate by contacting the exhaust gas with liquid from a cultivation pond. Certain approaches to cultivating algae and aquatic plants involve use of enclosed tubes or shallow troughs or ponds in which heat from sunlight raises the water temperature. Hence a heat stable carbonic anhydrase is particularly useful at the elevated cultivation temperatures.

Polynucleotides

The present invention also relates to isolated or synthetic polynucleotides encoding a polypeptide with carbonic anhydrase activity.

The techniques used to isolate or clone a polynucleotide encoding a polypeptide are known in the art and include isolation from genomic DNA, preparation from cDNA, or a combination thereof. The cloning of the polynucleotides from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Persephonella*, or another or related organism and thus, for example, may be an allelic or species variant of the polypeptide encoding region of the polynucleotide.

In a preferred embodiment the polynucleotides of the present invention are synthetic polynucleotides which have been codon optimized to increase the expression in a selected host cell. The host cell may be selected from the section "Host Cells" below. In a preferred embodiment the host cell is of the genus *Bacillus*, more preferably it is of the species *Bacillus subtilis*.

The techniques used to codon optimize a polynucleotide encoding a polypeptide are known in the art and described in for example WO 2006/066595 and Gustafsson et al., 2004, *Trends in Biotechnology* 22: 346-353.

The present invention also relates to an isolated or synthetic polynucleotide encoding a polypeptide having carbonic anhydrase activity, where the polynucleotide is selected from the group consisting of: a) a polynucleotide obtained by codon optimization of SEQ ID NO: 1 where the nucleotide sequence of the codon optimized polynucleotide is at least 60%, 65%, 70%, 75%, 80%, 85%, 90%, 91%, 92%, 93%, 94%, 95%, 96%, 97%, 98%, 99% identical to SEQ ID NO: 1; or b) a polynucleotide having a nucleotide sequence corresponding to nucleic acid residues 88 to 653 of SEQ ID NO: 3; or c) a polynucleotide which is at least 85%, 90%, 91%, 92%, 93%, 94%, 95%, 96%, 97%, 98%, 99% or 100% identical to nucleic acid residues 88 to 653 of SEQ ID NO: 3; or d) a fragment of (a) or (b) encoding a polypeptide having carbonic anhydrase activity.

In one aspect, the polynucleotide comprises or consists of SEQ ID NO: 3 or nucleic acid residues 88 to 653 of SEQ ID NO: 3 or a subsequence of SEQ ID NO: 3 that encode a fragment of SEQ ID NO: 4 having carbonic anhydrase activity.

Nucleic Acid Constructs

The present invention also relates to nucleic acid constructs comprising a polynucleotide of the present invention operably linked to one or more (several) control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter sequence, a polynucleotide that is recognized by a host cell for expression of a polynucleotide encoding a polypeptide of the present invention. The promoter sequence contains transcriptional control sequences that mediate the expression of the polypeptide. The promoter may be any polynucleotide that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *E. coli* lac operon, *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American*, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dana (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter including a gene encoding a neutral alpha-amylase in *Aspergilli* in which the untranslated leader has been replaced by an untranslated leader from a gene encoding triose phosphate isomerase in *Aspergilli*; non-limiting examples include modified promoters including the gene encoding neutral alpha-amylase in *Aspergillus niger* in which the untranslated leader has been replaced by an untranslated leader from the gene encoding triose phosphate isomerase in *Aspergillus nidulans* or *Aspergillus oryzae*); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), Saccharomyces cerevisiae triose phosphate isomerase (TPI), Saccharomyces cerevisiae metallothionein (CUP1), and Saccharomyces cerevisiae 3-phosphoglycerate kinase. Other useful promoters for yeast host cells are described by Romanos et al., 1992, Yeast 8: 423-488.

The control sequence may also be a suitable transcription terminator sequence, which is recognized by a host cell to terminate transcription. The terminator sequence is operably linked to the 3'-terminus of the polynucleotide encoding the polypeptide. Any terminator that is functional in the host cell of choice may be used in the present invention.

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, when transcribed is a nontranslated region of an mRNA that is important for translation by the host cell. The leader sequence is operably linked to the 5'-terminus of the polynucleotide encoding the polypeptide. Any leader sequence that is functional in the host cell of choice may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell of choice may be used.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, Mol. Cellular Biol. 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, Microbiological Reviews 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present at the N-terminus of a polypeptide, the propeptide sequence is positioned next to the N-terminus of a polypeptide and the signal peptide sequence is positioned next to the N-terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more (several) convenient restriction sites to allow for insertion or substitution of the polynucleotide encoding the polypeptide at such sites. Alternatively, the polynucleotide may be expressed by inserting the polynucleotide or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, chloramphenicol, kanamycin, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more (several) control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any gram-positive or gram-negative bacterium. Gram-positive bacteria include, but not limited to, *Bacillus, Clostridium, Enterococcus, Geobacillus, Lactobacillus, Lactococcus, Oceanobacillus,*

*Staphylococcus, Streptococcus*, and *Streptomyces*. Gram-negative bacteria include, but not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may, for instance, be effected by protoplast transformation (see, e.g., Chang and Cohen, 1979, *Mol. Gen. Genet.* 168: 111-115), by using competent cells (see, e.g., Young and Spizizen, 1961, *J. Bacteriol.* 81: 823-829, or Dubnau and Davidoff-Abelson, 1971, *J. Mol. Biol.* 56: 209-221), by electroporation (see, e.g., Shigekawa and Dower, 1988, *Biotechniques* 6: 742-751), or by conjugation (see, e.g., Koehler and Thorne, 1987, *J. Bacteriol.* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (Praha) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios* 68: 189-207, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. In a preferred aspect, the cell is of the genus *Persephonella*. In a more preferred aspect, the cell is *Persephonella marina, Persephonella hydrogeniphila* or *Persephonella guaymasensis*. In a most preferred aspect, the cell is *Persephonella marina* DSM 14350, *Persephonella hydrogeniphila* DSM 15103 or *Persephonella guaymasensis* DSM 14351.

The present invention also relates to methods of producing a polypeptide of the present invention, comprising: (a) cultivating a recombinant host cell of the present invention under conditions conducive for production of the polypeptide; and (b) recovering the polypeptide.

The host cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

In an alternative aspect, the polypeptides of the present invention can be produced from the host cell together with other polypeptides and/or fermentation products to provide a non-purified or minimally purified mixture that may be less expensive to produce than substantially pure polypeptides while still providing the desired carbonic anhydrase performance.

In an alternative aspect, the polypeptide is not recovered, but rather a host cell of the present invention expressing a polypeptide is used as a source of the polypeptide.

Compositions Comprising Polypeptides and Methods for their Preparation

The invention provides a composition comprising a *Persephonella* carbonic anhydrase of the present invention and preferably an excipient and a method for preparing such a composition comprising admixing the polypeptide of the invention with an excipient.

In a particular embodiment the *Persephonella* carbonic anhydrase of the invention is the major (polypeptide) component of the composition, e.g., a mono-component composition. In a mono-component composition the *Persephonella* carbonic anhydrase of the invention preferably constitutes at least 80% of the cabonica anhydrase activity, more preferably at least 90%, even more preferably at least 95% and most preferably 100% of the carbonic anhydrase activity. The excipient in this context is to be understood as any auxiliary agent or compound used to formulate the composition and includes solvent (e.g., water, inorganic salts, fillers, pigments, waxes), carriers, stabilizers, cross-linking agents, adhesives, preservatives, buffers and the like.

The composition may further comprise one or more additional enzymes, such as one or more additional carbonic anhydrases, a decarboxylase, laccase, or oxidase.

The compositions may be prepared in accordance with methods known in the art and may be in the form of a liquid or a solid composition. For instance, the enzyme composition may be formulated using methods known to the art of formulating technical enzymes and/or pharmaceutical products, e.g., into coated or uncoated granules or micro-granules. The polypeptide of the invention may thus be provided in the form of a granule, preferably a non-dusting granule, a liquid, in particular a stabilized liquid, a slurry or a protected polypeptide.

For certain applications, immobilization of the polypeptide may be preferred. An immobilized enzyme comprises two essential functions, namely the non-catalytic functions that are designed to aid separation (e.g., isolation of catalysts from the application environment, reuse of the catalysts and control of the process) and the catalytic functions that are designed to convert the target compounds (or substrates) within the time and space desired (Cao, Carrier-bound Immobilized Enzymes: Principles, Applications and Design, Wiley-VCH Verlag GmbH & Co. KGaA, Weinheim, Germany, 2005). When an enzyme is immobilized it is made insoluble to the target compounds (e.g., substrates) it aids converting and to the solvents used. An immobilized enzyme product can be separated from the application environment in order to facilitate its reuse, or to reduce the amount of enzyme needed, or to use the enzyme in a process where substrate is continuously delivered and product is continuously removed from proximity to the enzyme, which, e.g., reduces enzyme cost. Furthermore, enzymes are often stabilized by immobilization. A process involving immobilized enzymes is often continuous, which facilitates easy process control. The immobilized enzyme can be retained as a heterogeneous catalyst by mechanical means, or by inclusion in a definite space. The latter can be done by micro-encapsulation, e.g., in semi permeable membranes or by inclusion in UF systems using, e.g., hollow fiber modules, etc. Immobilization on porous carriers is also commonly used. This includes binding of the enzyme to the carrier, e.g., by adsorption, complex/ionic/covalent binding, or just simple absorption of soluble enzyme on the carrier and subsequent removal of solvent. Cross-linking of the enzyme can also be used as a means of immobilization. Immobilization of enzyme by inclusion into a carrier is also industrially applied. (Buchholz et al., Biocatalysts and Enzyme Technology, Wiley-VCH Verlag GmbH & Co. KGaA, Weinheim, Germany, 2005). Specific methods of immobilizing enzymes such as carbonic anhydrase include, but are not limited to, spraying of the enzyme together with a liquid medium comprising a polyfunctional amine and a liquid medium comprising a cross-linking agent onto a particulate porous carrier as described in WO 2007/036235 (hereby incorporated by reference), linking of carbonic anhydrase with a cross-linking agent (e.g., glutaraldehyde) to an ovalbumin layer which in turn adhere to an adhesive layer on a polymeric support as described in WO 2005/114417 (hereby incorporated by reference), or coupling of carbonic anhydrase to a silica carrier as described in U.S. Pat. No. 5,776,741 or to a silane, or a CNBr activated carrier surface such as glass, co-polymerization of carbonic anhydrase with methacrylate on polymer beads as described in Bhattacharya et al., 2003, *Biotechnol. Appl. Biochem.* 38: 111-117 (hereby incorporated by reference), or using globular protein and adhesive as described in US 2010/0068784. The carbonic anhydrase may also be immobilized using tags such as histidine-like tags (e.g., 6×His tag or HQ tag) or a cellulose binding module (CBM) (Liu et al, 2008, *Biotechnol. Prog.* 25: 68-74).

An embodiment of the present invention is a composition comprising a matrix suitable for immobilization and a carbonic anhydrase selected from the group consisting of
  (a) derived from or producible by *Persephonella marina* DSM 14350; or
  (b) a polypeptide having an amino acid sequence corresponding to amino acid residues 20 to 243 of SEQ ID NO: 2 or amino acid residues 29 to 251 of SEQ ID NO: 4; or
  (c) a polypeptide which is at least 60%, 65%, 70%, 75%, 80%, 85%, 90%, 91%, 92%, 93%, 94%, 95%, 96%, 97%, 98% or 99% identical to amino acid residues 20 to 243 of SEQ ID NO: 2 or amino acid residues 29 to 251 of SEQ ID NO: 4; or
  (d) a fragment of (a), (b) or (c) having carbonic anhydrase activity; or
  (e) a polypeptide encoded by a nucleic acid sequence which hybridizes under, very low, low, medium, medium-high or high stringency conditions with:
    (i) a polynucleotide sequence encoding a mature polypeptide of SEQ ID NO: 2 or SEQ ID NO: 4; or
    (ii) a polynucleotide sequence of SEQ ID NO: 1 or SEQ ID NO: 3; or
    (iii) a subsequence of (i) or (ii), of at least 100 contiguous nucleotides, or
    (iv) a complementary strand of (i) or (ii); or
  (f) a polypeptide encoded by a nucleic acid sequence which, because of the degeneracy of the genetic code, does not hybridize with the polynucleotide sequence of SEQ ID NO: 1 or SEQ ID NO: 3, but which codes for a polypeptide having an amino acid sequence according to b) or c); or
  (g) a polypeptide encoded by a nucleic acid sequence which is at least 60%, 65%, 70%, 75%, 80%, 85%, 90%, 91%, 92%, 93%, 94%, 95%, 96%, 97%, 98% or 99% identical to SEQ ID NO: 1 or SEQ ID NO: 3.

In a further embodiment of the present invention the carbonic anhydrase is immobilized on a matrix. The matrix may for example be selected from the group beads, fabrics, fibers, hollow fibers, membranes, particulates, porous surfaces, rods, structured packing, and tubes. Specific examples of suitable matrices include alumina, bentonite, biopolymers, calcium carbonate, calcium phosphate gel, carbon, cellulose, ceramic supports, clay, collagen, glass, hydroxyapatite, ion-exchange resins, kaolin, nylon, phenolic polymers, polyaminostyrene, polyacrylamide, polypropylene, polymerhydrogels, sephadex, sepharose, silica gel, precipitated silica, and TEFLON-brand PTFE. In an embodiment of the present invention carbonic anhydrase is immobilized on a nylon matrix according to the techniques described in Methods in Enzymology volume XLIV (section in the chapter: Immobilized Enzymes, pages 118-134, edited by Klaus Mosbach, Academic Press, New York, 1976), hereby incorporated by reference.

The polypeptide to be included in the composition may be stabilized in accordance with methods known in the art e.g., by stabilizing the polypeptide in the composition by adding an antioxidant or reducing agent to limit oxidation of the polypeptide or it may be stabilized by adding polymers such as PVP, PVA, PEG, sugars, oligomers, polysaccharides or other suitable polymers known to be beneficial to the stability of polypeptides in solid or liquid compositions or it may be stabilized by adding stabilizing ions, such as zinc (e.g., zinc chloride or zinc sulphate) which is present in the enzyme active site. A preservative, such as Proxel, or penicillin, can be added to extend shelf life or performance in application.

In embodiments of the present invention the carbonic anhydrase is immobilized by adsorption onto a matrix, surface or substrate. Non-limiting examples of a matrix, surface or substrate include those from the group: beads, fabrics, fibers, hollow fibers, membranes, particulates, porous surfaces, rods, structured packing, and tubes. Specific examples of suitable matrices, surfaces or substrates include alumina, bentonite, biopolymers, calcium carbonate, calcium phosphate gel, carbon, cellulose, ceramic supports, clay, collagen, glass, hydroxyapatite, ion-exchange resins, kaolin, nylon, phenolic polymers, polyaminostyrene, polyacrylamide, polyacrylonitrile (acrylic), polyethylene, polypropylene, polyester, polyurethane, polymerhydrogels, sephadex, sepharose, silica gel, precipitated silica, and TEFLON-brand PTFE. In embodiments, the matrices, surfaces or substrates may be dried after adsorption of the enzyme.

In a further embodiment the composition of the invention is a composition applicable in the capture of carbon dioxide.

EXAMPLES

Example 1

Cloning and Expression of *Persephonella marina* DSM 14350 Carbonic Anhydrase in *B. subtilis*

*Persephonella marina* is a marine bacterium that grows at around 80° C. (Gotz, et al., 2002, *International Journal of Systematic and Evolutionary Microbiology* 52: 1349-1359).

A synthetic gene based on the protein sequence of *Persephonella marina* DSM 14350 carbonic anhydrase (UniProt accession nr. C0QRB5) was designed and the gene codon usage was optimized for *B. subtilis*.

The codon optimization process designed a gene using synonymous codons proportional to the frequencies in the codon table in table 1 below. This method is known in the art, see for example Gustafsson et al, 2004, *Trends in Biotechnology* 22: 346-353.

TABLE 1

| B. subtilis codon frequencies | | |
|---|---|---|
| #Codon | Amino acid | Frequency |
| GCA | A | 0.182 |
| GCC | A | 0 |
| GCG | A | 0.182 |
| GCT | A | 0.636 |
| TGC | C | 0.5 |
| TGT | C | 0.5 |
| GAC | D | 1 |
| GAT | D | 0 |
| GAA | E | 0.13 |
| GAG | E | 0.87 |
| TTC | F | 0.75 |
| TTT | F | 0.25 |
| GGA | G | 0 |
| GGC | G | 0.833 |
| GGG | G | 0 |
| GGT | G | 0.167 |
| CAC | H | 0.5 |
| CAT | H | 0.5 |
| ATA | I | 0 |
| ATC | I | 1 |
| ATT | I | 0 |

TABLE 1-continued

| B. subtilis codon frequencies | | |
|---|---|---|
| #Codon | Amino acid | Frequency |
| AAA | K | 0.652 |
| AAG | K | 0.348 |
| CTA | L | 0 |
| CTC | L | 0 |
| CTG | L | 0 |
| CTT | L | 1 |
| TTA | L | 0 |
| TTG | L | 0 |
| ATG | M | 1 |
| AAC | N | 0.9 |
| AAT | N | 0.1 |
| CCA | P | 0.077 |
| CCC | P | 0 |
| CCG | P | 0 |
| CCT | P | 0.923 |
| CAA | Q | 0.8 |
| CAG | Q | 0.2 |
| AGA | R | 0 |
| AGG | R | 0 |
| CGA | R | 0 |
| CGC | R | 1 |
| CGG | R | 0 |
| CGT | R | 0 |
| AGC | S | 0 |
| AGT | S | 0 |
| TCA | S | 0.222 |
| TCC | S | 0 |
| TCG | S | 0 |
| TCT | S | 0.778 |
| ACA | T | 0.2 |
| ACC | T | 0 |
| ACG | T | 0 |
| ACT | T | 0.8 |
| GTA | V | 0.429 |
| GTC | V | 0 |
| GTG | V | 0 |
| GTT | V | 0.571 |
| TGG | W | 1 |
| TAC | Y | 0.667 |
| TAT | Y | 0.333 |
| TAA | * | 1 |
| TAG | * | 0 |
| TGA | * | 0 |

The alpha-amylase signal peptide from *B. licheniformis*, which is encoded by the nucleotide sequence: atgaaacaacaaaaacggctttacgcccgattgctgacgctgttatttgcgct-catcttcttgctgcctcattctgcagcagcggcg (SEQ ID NO: 5) was cloned in frame to the DNA encoding the optimized carbonic anhydrase gene. The nucleotide sequence of the fusion product corresponds to SEQ ID NO: 3.

The synthetic CA gene SEQ ID NO: 3 was purchased in an *E. coli* vector (selected by the synthetic gene vendor) and the CA gene was re-cloned into a suitable vector resulting in plasmid C6221.

Figure 3:
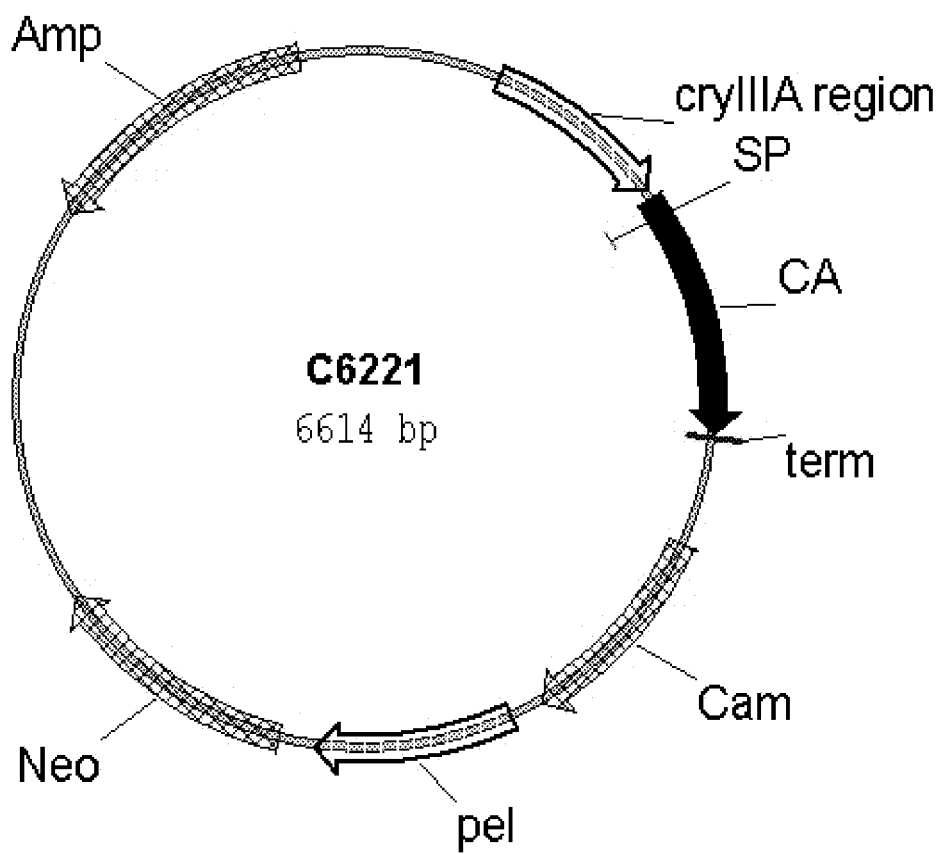
FIG. 3 is a schematic presentation of cloning plasmid C6221. The abbreviations in the figure are described below. "CA" is the codon optimized carbonic anhydrase encoding gene. "SP" is the alpha-amylase signal peptide from *B. licheniformis*. "Term" is the terminator sequence. "Cam" is the gene coding for chloramphenicol acetyltransferase. "pel"

A plasmid map of C6221 containing optimized CA gene *Persephonella marina* (denoted CA) is shown in FIG. 3. The CA gene was expressed by control of a triple promoter system consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence (denoted cryIIIA in FIG. 3). The expression cassette has also been described in WO 99/43835. Furthermore, plasmid C6221 contained a terminator (term) sequence, a gene coding for chloramphenicol acetyltransferase (cam) which was used as selection maker (as described in (Diderichsen et al., 1993, *Plasmid* 30: 312-315) for *B. subtilis*. The beta-lactamase gene (amp) giving ampicillin resistance as well as a kanamycin resistance gene (neo) were used as cloning selection marker genes for *E. coli* growth. The plasmid also contained an *E. coli* origin of replication.

*E. coli* TOP10 cells were transformed with plasmid C6221 and one correct clone was selected using methods known in the art. Competent *B. subtilis* cells were transformed with the plasmid isolated from the selected *E. coli* clone, the CA gene construct in the plasmid integrated into the *Bacillus subtilis* chromosome by homologous recombination into the pectate lyase gene locus (denoted pel in FIG. 3).

Chloramphenicol resistant *B. subtilis* clones were analyzed by DNA sequencing to verify the correct DNA sequence of the construct. The translated protein sequence corresponds to SEQ ID NO: 4, where amino acid 1-28 corresponds to the alpha-amylase signal peptide from *B. licheniformis*, the amino acid alanine in position 29 was added to optimize the signal peptide cleavage site and amino acids 29 to 251 corresponds to the predicted mature carbonic anhydrase.

One expression clone was selected and was cultivated on a rotary shaking table in 500 ml baffled Erlenmeyer flasks each containing 100 ml casein based media supplemented with 34 mg/l chloramphenicol. The clone was cultivated for 5 days at 37° C. It was determined that there was very high carbonic anhydrase activity in the culture broth solution according to Wilbur, 1948, *J. Biol. Chem.* 176: 147-154 (essentially as described in Example 2).

To semi-purify the heat-stable CA from endogenous *B. subtilis* enzymes in the culture broth, the cell free broth was incubated at 80° C. for 15 min and the solution was centrifuged for 30 min at 15.000×g. The sterile filtered supernatant (0.2 μm filter, Whatman) had a CA activity of 166000 WAU/ml determined as described in example 2.

Example 2

Detection of Carbonic Anhydrase Activity

The test for the detection of carbonic anhydrase was described by Wilbur, 1948, *J. Biol. Chem.* 176: 147-154. The set up is based on the pH change of the assay mixture due to the formation of bicarbonate from carbon dioxide as given in equation 1:

[$CO_2 + H_2O \rightarrow HCO_3^- + H^+$].

The activity assay used in this study was derived from the procedure of Chirica et al., 2001, *Biochim. Biophys. Acta* 1544 (1-2): 55-63. A solution containing approximately 60 to 70 mM $CO_2$ was prepared by bubbling $CO_2$ at a flow rate of 100 ml/min into 100 ml distilled water using the tip of a syringe approximately 30 minutes prior to the assay. The $CO_2$ solution was chilled in an icewater-bath at 0-4° C. To test for the presence of carbonic anhydrase, 2 ml of 25 mM Tris-HCl solution adjusted to pH 8.3 with 25 mM HCl (containing sufficient bromothymol blue to give a distinct and visible blue color) were added to two 13×100 mm test tubes chilled in 4° C. water-bath. To one tube, 10 microliters of the enzyme containing solution was added, and an equivalent amount of deionized water was added to the second tube to serve as a control. 2 ml of $CO_2$ solution was added very quickly and smoothly to the bottom of each tube. Simultaneously with the addition of the $CO_2$ solution, a stopwatch was started. The time required for the solution to change from blue to yellow was recorded (transition point of bromothymol blue is pH 6-7.6). The production of hydrogen ions during the $CO_2$ hydration reaction lowers the pH of the solution until the color transition point of the bromothymol blue is reached. The time required for the color change is inversely related to the quantity of carbonic anhydrase present in the sample. The tubes must remain immersed in the ice bath for the duration of the assay for results to be reproducible. Typically, the uncatalyzed reaction (the control) takes 40 to 150 seconds for the color change to occur, whereas the enzyme catalyzed reaction is complete between 5 and 20 seconds, depending upon the amount of enzyme protein in the enzyme solution added and depending on the residual activity after heat treatment (see Example 1). Detecting the color change is somewhat subjective but the error for triple measurements was in the range of 0 to 1 sec difference for the catalyzed reaction. One unit is defined after Wilbur [1 U=(1/tc)−(1/tu)×1000] where U is units and tc and to represent the time in seconds for the catalyzed and uncatalyzed reaction, respectively (Wilbur, 1948, *J. Biol. Chem.* 176: 147-154). These units are also termed Wilbur-Anderson units (WAU).

Example 3

Heat-Stability of *P. marina* Carbonic Anhydrase

The activity of the recombinant carbonic anhydrase after treatment at increased temperature was assessed.

The thermal stability of CA enzyme obtained from Example 1 was measured as follows: the solution obtained in Example 1 was diluted in 1 M $NaHCO_3$, pH 8 to give 2500 WAU and was incubated for 15 minutes at desired temperature. To measure tu, 1 M $NaHCO_3$ was heated at the same temperature. This corresponds to the reaction time for the uncatalyzed reaction as explained in Example 2. The samples were cooled down in an ice-water bath and the carbonic anhydrase activity was measured using the Wilbur-Anderson assay described in Example 2.

The residual activity after incubation at elevated temperatures was calculated as the activity after heat-treatment divided by the activity of enzyme at 25° C. prior to the treatment times 100%. The results are presented in Table 2. The data for *M. thermophila* CA were taken from Table 1 in WO 2010/151787 (application no. PCT/US2010/040022). The data clearly shows that *P. marina* CA was superior in terms of short term thermostability over *M. thermophila* CA.

TABLE 2

Temperature stability after 15 min heat treatment in 1M $NaHCO_3$

| | Temperature [° C.] | | | | | | | | | | |
|---|---|---|---|---|---|---|---|---|---|---|---|
| CA | 25 | 37 | 50 | 55 | 60 | 65 | 70 | 75 | 80 | 90 | 100 |
| | Residual activity [%] | | | | | | | | | | |
| *P. marina* | 100 ± 33 | n.d | Nd | n.d. | 100 ± 33 | n.d. | n.d. | n.d. | 109 ± 37 | 85 ± 28 | 37 ± 15 |
| *M. thermophila* | 100 | 98 | 92 | n.d. | 79 | n.d. | 77 | n.d. | 17 | n.d | n.d | n.d. = not determined

Stability as a Function of Increasing Incubation Time

The carbonic anhydrase solution obtained from Example 1 was diluted 10 times with 1 M $NaHCO_3$ pH 8 and heated at 80° C. for the indicated time. The residual activity was measured as described above. The results are presented in Table 3. The data for *M. thermophila* CA were taken from Table 1 in WO 2010/151787 (application no. PCT/US2010/040022). The data clearly shows that *P. marina* carbonic anhydrase has not lost its activity in 1 M $NaHCO_3$ buffer after incubation at 80° C. for 2 hours at pH 8.

TABLE 3

Residual activity after heat treatment at 80° C.

| CA | Time [min] | | | | | | |
|---|---|---|---|---|---|---|---|
| | 0 | 15 | 30 | 45 | 60 | 90 | 120 |
| | Residual activity [%] | | | | | | |
| *P. marina* | 100 ± 28 | 117 ± 33 | 118 ± 33 | 129 ± 36 | 129 ± 36 | 109 ± 30 | 101 ± 28 |
| *M. thermophila* | 100 | 19 | 0 | n.d. | n.d. | n.d. | n.d. | n.d. = not determined

Stability as a Function of pH

The carbonic anhydrase solution obtained from Example 1 was diluted 10 times with 0.1 M Britton-Robinson buffer, adjusted to the pH indicated in Table 4, and heated at 50° C. for the indicated time. The residual activity was measured as described above. The results are presented in Table 4. The data shows that *P. marina* carbonic anhydrase retains greater than 80% activity when heated at 50° C. for 1 day in 0.1 M Britton-Robinson buffer over the broad pH range 4-11, and maintains full activity over the pH range 6-11. After 10 days heating at 50° C., *P. marina* carbonic anhydrase retains greater than 50% activity over the pH range 5-11.

TABLE 4

Residual activity at different pH after heat treatment at 50° C.

| Time | pH | | | | | | | |
|---|---|---|---|---|---|---|---|---|
| | 4 | 5 | 6 | 7 | 8 | 9 | 10 | 11 |
| | Residual activity [%] | | | | | | | |
| 1 day | 82 | 94 | 102 | 102 | 102 | 102 | 102 | 101 |
| 10 days | 44 | 73 | 54 | 64 | 64 | 64 | 61 | 58 |

Example 4

Extraction of $CO_2$ from a Mixed Gas Stream in a Hollow Fiber Membrane Bioreactor A lab-scale hollow fiber membrane bioreactor (HFMB) was set up to selectively capture $CO_2$ from a gas stream which could resemble a flue gas.

Hollow Fiber Membrane Bioreactor Set-Up

Porous hydrophobic hollow fiber membranes provide a high surface area of contact between the gas stream and carrier liquid. As a result they facilitate carbonation of a liquid or removal of $CO_2$ from a liquid. The selected module consists of 2300 parallel hollow fibers with 0.18 $m^2$ active surface area and average pore size of 0.01×0.04 micron (Liqui-cel® MiniModule® 1×5.5 purchased from Membrana, N.C., USA). These membranes are easy to scale-up to industrial scale and have been used in industry for wastewater treatment and beverage carbonation. A schematic drawing of the bioreactor set-up is shown in FIG. 1. In the set-up carrier liquid was passed through the hollow fibers lumen using a positive displacement pump. The liquid flow rate was set to about 4 ml/min. The gas stream containing a mixture of 15% $CO_2$ (9 CCM) and 85% $N_2$ (51 CCM) (feed gas) entered the feed side of the hollow fibers counter-currently to the carrier liquid stream and the treated gas stream (scrubbed gas) exited the module at the sweep side of the hollow fibers. Two mass flow controllers were used to mix nitrogen and carbon dioxide with consistent concentration throughout the experiments. A mass flow meter was used to monitor the flow of the scrubbed gas as it exits the reactor. The gas and liquid flows and pressures were adjusted to avoid entering liquid to the gas phase and gas bubbles in the liquid phase of the module.

The purpose of this set-up was to demonstrate absorption of $CO_2$ into carrier liquid which results in hydration of $CO_2$ to bicarbonate. The absorption was measured by analyzing the $CO_2$ concentration in feed gas and scrubbed gas using a gas chromatograph (GC).

Carrier Liquid

A 0.5 M sodium bicarbonate adjusted to pH 9 with 0.5 M sodium hydroxide solution was used as a carrier liquid control. Then, 2500 WAU/ml of carbonic anhydrase (CA) enzyme protein obtained in Example 1 was added to the reservoir. The temperature was maintained at room temperature.

Gas Chromatography Method (GC-TCD)

A Shimadzu 2010 gas chromatograph with a thermal conductivity detector and a gas sampling valve was used for $CO_2$ concentration measurement. A capillary Carboxen Plot 1010 column was used to detect nitrogen and carbon dioxide. The column was heated isothermally for 7 minutes at 35° C., the temperature was increased with 20° C./min rate to 200° C. and it was maintained at 200° C. for 2 minutes. Injector and detector temperatures were maintained at 230° C. Column flow is 1 ml/min, split ratio 10 to 1 and carrier gas was helium. Nitrogen and carbon dioxide peaks were detected at retention times 6.4 and 15.3 minutes, respectively. The $CO_2$ peak was calibrated using three carbon dioxide standards with 0.1%, 1% and 10% by weight carbon dioxide in nitrogen purchased from Scott Specialty gases (Pennsylvania, USA).

Results

Table 5 shows the data collected from GC using carrier liquid with or without carbonic anhydrase. Each data point is the measurement from each injection during run time at room temperature. Data from the first injection from each set of measurements (carrier liquid with or without carbonic anhydrase) was disregarded to eliminate doubt about residual gas remained in the tubing or columns. The results indicate that 2500 WAU carbonic anhydrase enzyme protein from *P. Marina* increases the efficiency of $CO_2$ removal to about 61.9% compared to a control run at the same conditions without enzyme (~25.1%). Percent $CO_2$ in feed gas was averaged to be 15.8%.

TABLE 5

Effect of carrier liquid on the $CO_2$ concentration of the gas stream exiting the hollow fiber membrane bioreactor

| Carrier liquid | pH in reservoir | % $CO_2$ in Scrubbed gas (avg) | % $CO_2$ removed (avg) |
|---|---|---|---|
| 0.5M $NaHCO_3$ | 9.0 | 11.9 ± 0.6 | 25.1 ± 0.6 |
| 0.5M $NaHCO_3$ + 2500 WAU CA | 9.0 | 6.0 ± 0.5 | 61.9 ± 1.6 |

Example 5

Heat Stability of *P. marina* Carbonic Anhydrase in 3 M Potassium (Bi-)Carbonate The activity of the recombinant carbonic anhydrase was measured after treatment in high ionic strength aqueous potassium (bi-)carbonate solutions at ambient and elevated temperature for extended time. Carbonic anhydrase enzyme solution obtained as in Example 1 was diluted 10-fold in either 3 M aqueous potassium bicarbonate ($KHCO_3$) at pH 8.5, or in 3 M aqueous potassium carbonate ($K_2CO_3$), adjusted to pH 11 using approximately one part 3 M $KHCO_3$ to two parts 3 M $K_2CO_3$, to give the initial enzyme solution activities shown in Table 6. Initial enzyme activity (WAU) was measured at time 0 hours as described in Example 2. De-ionized water diluted 10-fold in either 3 M $KHCO_3$ or 3 M $K_2CO_3$ was used to measure the time for the corresponding uncatalyzed reaction (tu) as explained in Example 2, and these solutions were subsequently treated at the same conditions as the enzyme-containing solutions. Solutions in sealed vials were placed in either a water bath at 80° C. or allowed to sit at room temperature (23° C.). Samples for WAU analysis were taken at 0, 6 and 24 hours for the 80° C. bath samples and at 0 and 72 hours for the room temperature samples. Carbonic anhydrase activity was measured using the Wilbur-Anderson assay described in Example 2. In the WAU measurements of the present example, in order to shorten the tc time to within 40-60 seconds, the amount of $CO_2$ solution added to assay tubes for the analysis of 3 M $KHCO_3$-based samples was 3 ml and the amount of $CO_2$ solution added to assay tubes for the analysis of 3 M $K_2CO_3$-based samples was 4 ml. The final pH of test solutions were measured using pH paper at the end of the experiment. As expected, the final pH of treatments was higher than the initial pH, due to that bicarbonate-based solutions release $CO_2$ to air over time, which is a well-known phenomenon. Therefore, without being bound by any particular theory, in addition to high temperature, a contributing factor to the loss of enzyme activity at longer times could be high pH. The fact that *P. marina* CA retains activity after the demanding conditions of this test demonstrates that *P. marina* CA is a particularly stable carbonic anhydrase.

The percent remaining activity after incubation was calculated as the activity after treatment divided by the activity at 0 hr, prior to incubation, times 100%. Results presented in Table 6 show that *P. marina* CA retains significant enzyme activity over extended time in conditions of high pH, high ionic strength, and elevated temperature.

TABLE 6

Residual activity after treatment in 3M (bi-)carbonate solvents at 23° C. and 80° C.

| Solvent | Initial enzyme activity (WAU) | Temp (° C.) | Treatment time (hours) | | | | Final pH |
|---|---|---|---|---|---|---|---|
| | | | 0 | 6 | 24 | 72 | |
| | | | Residual activity (%) | | | | |
| 3M $KHCO_3$ | 190 | 23 | 100 | n.d. | n.d. | 101 | 9 |
| 3M $KHCO_3$ | 142 | 80 | 100 | 84 | 50 | n.d. | 11 |
| 3M $K_2CO_3$ | 76 | 23 | 100 | n.d. | n.d. | 20 | 13 |
| 3M $K_2CO_3$ | 76 | 80 | 100 | 33 | 8 | n.d. | 12 | n.d. = not determined

Example 6

Enzyme Stability to Ultrasonic Agitation

Ultrasonic agitation could be useful for certain $CO_2$ gas separation processes. The activity of two different carbonic anhydrases (CA) was measured before and after exposure to ultrasonic agitation. *P. marina* CA enzyme solution was obtained as described in Example 1. Lyophilized Bovine CA (Sigma-Aldrich, catalog nr. C3934) was dissolved in de-ionized water before use. Each enzyme solution was diluted 10-fold in 1 M aqueous sodium bicarbonate ($NaHCO_3$), pH 8.5. De-ionized water diluted 10-fold in 1 M $NaHCO_3$ was used to measure the time for the uncatalyzed reaction (tu) as explained in Example 2, and this solution was treated at the same conditions as the enzyme-containing solutions. Samples were placed in sealed vials in a sonic waterbath (Branson 8510, 40 kHz frequency, 320 W) at 50° C. Samples were taken at 0, 2 and 6 hours and activity was tested using the Wilbur-Anderson assay described in Example 2.

The percent residual activity after treatment was calculated as the activity after treatment divided by the activity at time 0 hr times 100%. Results presented in Table 7 show that *P. marina* CA retained high activity after the treatment whereas Bovine CA was inactivated after the 6 hour treatment, irrespective of the temperature.

TABLE 7

Residual enzyme activity after treatment with and without sonication.

| Enzyme Initial activity (WAU) | | *P. marina* CA 153 | Bovine CA 115 |
|---|---|---|---|
| Temperature (° C.) | Time (hr) | Residual activity (%) | |
| 35 | 0 | 100 | 100 |
| 35 | 2 | 82 | 88 |
| 35 | 6 | 100 | 4 |
| 50 | 0 | 100 | 100 |
| 50 | 2 | 79 | 40 |
| 50 | 6 | 97 | 0 |

Example 7

Heat Stability of Carbonic Anhydrases in Different Solvents at Extended Time

The activity of two recombinant carbonic anhydrases (CA) was measured after treatment at elevated temperature for extended time in aqueous solutions that could be used for $CO_2$ gas separation processes. *B. clausii* CA was obtained and purified as described in Examples 1 and 3 of WO 2008/095057 (herein incorporated by reference). *P. marina* CA enzyme solution obtained as in Example 1 was further purified using a cationic ion exchange column at pH 6 (purified *P. marina* CA). Each purified enzyme solution was further diluted 10-fold in each of three solvents: 1.5 M aqueous potassium bicarbonate ($KHCO_3$) at pH 8.6; 1.5 M aqueous N-methyldiethanolamine (MDEA) at pH 10.7; or a solution containing 1.5 M $KHCO_3$/1.5 M MDEA at pH 9.8, prepared by mixing equal volumes of 3 M $KHCO_3$ and 3 M MDEA. Initial enzyme activity (WAU) of each solution was measured as described in Example 2 after allowing the enzyme-solvent mixtures to stand at room temperature (23° C.) for 5 hours. De-ionized water diluted 10-fold in each solvent was used to measure the time for the corresponding uncatalyzed reaction (tu) as explained in Example 2, and these solutions were subsequently treated at the same conditions as the enzyme-containing solutions. Solutions in sealed vials were placed in a water bath at 80° C. for 13 hours. Samples were removed and chilled on ice until activity analysis. Carbonic anhydrase activity was measured using the Wilbur-Anderson assay described in Example 2, except that the amount of $CO_2$ solution added to each assay tube was 4.8 ml, which resulted in tu times of 20-40 seconds. The final pH of each test solution was measured using pH paper (+/−0.5 pH unit accuracy). The pH results are shown in Table 8.

The percent remaining activity after incubation was calculated as the activity after treatment divided by the initial activity times 100%. Results presented in Table 8 show that *P. marina* CA retains higher activity compared to *B. clausii* CA over extended time in conditions of high pH, high ionic strength, and elevated temperature. The measured initial activities demonstrate that both enzymes retain activity in all three solvents for several hours at room temperature. It was observed that *P. marina* CA retained higher activity in the combination of $KHCO_3$/MDEA than in MDEA alone, even though the final pH of the $KHCO_3$/MDEA combination was higher. This, combined with the higher activity in the $KHCO_3$ solvent, suggests that carbonic anhydrase is stabilized in the presence of bicarbonate and that including bicarbonate in $CO_2$ separation solvents containing carbonic anhydrase is beneficial.

TABLE 8

Residual activity after treatment in three solvents at 80° C. for 13 hours.

| Solvent | Enzyme | Initial activity (WAU) | Final pH | Residual activity (%) |
|---|---|---|---|---|
| 1.5M $KHCO_3$ | *P. marina* CA | 288 | 9 | 69 |
| | *B. clausii* CA | 108 | 9 | 0 |
| 1.5M $KHCO_3$/ 1.5M MDEA | *P. marina* CA | 172 | 11 | 14 |
| | *B. clausii* CA | 64 | 11 | 2 |
| 1.5M MDEA | *P. marina* CA | 149 | 10.5 | 1 |
| | *B. clausii* CA | 61 | 10.5 | 0 | n.d. = not determined

Example 8

Heat Stability of Carbonic Anhydrase in Different Solvents

The activity of recombinant *P. marina* carbonic anhydrase (CA) obtained as in Example 1 was measured after treatment at elevated temperatures in aqueous solutions that could be used for $CO_2$ gas separation processes. The enzyme solution was further diluted 10-fold in each of the following solvents: 1.5 M aqueous potassium bicarbonate ($KHCO_3$) at pH 8.6; 1.5 M aqueous N-methyldiethanolamine (MDEA) at pH 10.7; a solution containing 1.5 M $KHCO_3$/1.5 M MDEA at pH 9.8, prepared by mixing equal volumes of 3 M $KHCO_3$ and 3 M MDEA; 1.5 M $K_2HPO_4$ at pH 10.3; a solution containing 1.5 M $KHCO_3$/1.5 M $K_2HPO_4$ at pH 9, prepared by mixing equal volumes of 3 M $KHCO_3$ and 3 M $K_2HPO_4$; 1.5 M tris(hydroxymethyl)aminomethane (TRIS) at pH 10.5; and 1.5 M $KHCO_3$/1.5 M TRIS at pH 9.6, prepared by mixing equal volumes of 3 M $KHCO_3$ and 3 M TRIS. Initial enzyme activity (WAU) of each solution was measured as described in Example 2. De-ionized water diluted 10-fold in each solvent was used to measure the time for the corresponding uncatalyzed reaction (tu) as explained in Example 2, and these solutions were subsequently treated at the same conditions as the enzyme-containing solutions. Solutions in sealed vials were placed in a water bath at 50° C. for 1 hour. Samples were removed and chilled on ice until activity analysis. Carbonic anhydrase activity was measured using the Wilbur-Anderson assay described in Example 2, except the amount of $CO_2$ solution added to each assay tube was adjusted to ensure tu times between 30-60 seconds. For solvents 1.5 M $KHCO_3$, 1.5 M $KHCO_3$/1.5 M MDEA and 1.5 M MDEA, 3.5 ml $CO_2$ solution was added. For solvents 1.5 M TRIS, 1.5 M $KHCO_3$/1.5 M TRIS, 1.5 M $K_2HPO_4$ and 1.5 M $KHCO_3$/1.5 M $K_2HPO_4$ 4 ml $CO_2$ solution was added. It was observed that the color transition of the assay pH indicator was broad (blue to greenish-yellow to yellow) in the case of the $K_2HPO_4$-containing solvents. This is due to the high buffering capacity of phosphate-based solutions, which could be beneficial in certain $CO_2$ gas separation processes. After activity analysis, the samples were placed in a water bath at 80° C. for 1 hour, then removed and chilled on ice until activity analysis, which was carried out as described above. The final pH of each test solution was measured using pH paper. The pH results are shown in Table 9.

The percent remaining activity after incubation was calculated as the activity after treatment divided by the initial activity times 100%. Results presented in Table 9 show that *P. marina* CA retains almost full activity in all the solvents after treatment for 1 hr at 50° C., and retains high activity in 1.5 M $KHCO_3$ and 1.5 M $KHCO_3$/1.5 M MDEA after an additional 1 hr at 80° C. *P. marina* CA retains high activity in 1.5 M $KHCO_3$/1.5 M $K_2HPO_4$, 1.5 M $K_2HPO_4$, and 1.5 M $KHCO_3$/1.5 M TRIS after an additional 1 hr at 80° C. However, *P. marina* CA was inactivated by treatment at 80° C. in 1.5 M MDEA and 1.5 M Tris. It was observed that the largest change in pH of the solvents occurred for the 1.5 M $KHCO_3$/1.5 M MDEA combination, the 1.5 M $KHCO_3$/1.5 M $K_2HPO_4$ combination, and the 1.5 M $KHCO_3$/1.5 M TRIS combination, suggesting that $CO_2$ was most easily released from these solvents, which could be beneficial for the desorption stage of a $CO_2$ gas separation process. *P. marina* CA retained higher activity in the combination of $KHCO_3$/MDEA than in MDEA alone as well as in 1.5 M $K_2HPO_4$, 1.5 M $KHCO_3$/1.5 M $K_2HPO_4$ and 1.5 M $KHCO_3$/1.5 M TRIS even though the final pH of these combinations was higher.

TABLE 9

Residual activity after treatment in aqueous solvents at 50° C. then 80° C.

| Solvent | Initial activity (WAU) | Residual activity (%), after 1 hour at 50° C. | pH after treatment | Residual activity (%), after 1 additional hour at 80° C. | Final pH |
|---|---|---|---|---|---|
| 1.5M KHCO$_3$ | 170 | 101 | 9 | 98 | 9 |
| 1.5M KHCO$_3$/ 1.5M MDEA | 122 | 95 | 11 | 74 | 11 |
| 1.5M MDEA | 126 | 91 | 10 | 0 | 10 |
| 1.5M K$_2$HPO$_4$ | 190 | 93 | 10 | 87 | 10 |
| 1.5M KHCO$_3$/ 1.5M K$_2$HPO$_4$ | 178 | 106 | 11 | 98 | 11 |
| 1.5M TRIS | 94 | 97 | 10 | 2 | 11 |
| 1.5M KHCO$_3$/ 1.5M TRIS | 117 | 83 | 11 | 82 | 11 |

The invention claimed is:

1. A method for extracting carbon dioxide comprising:
   treating a carbon dioxide-containing medium with a carbonic anhydrase in a reactor to produce a treated medium, and
   removing said treated medium from said reactor, thereby extracting said carbon dioxide:
   wherein said carbonic anhydrase is a polypeptide having at least 95% sequence identity to amino acid residues 20 to 243 of the amino acid sequence of SEQ ID NO: 2 or having at least 95% sequence identity to amino acid residues 29 to 251 of the amino acid sequence of SEQ ID NO: 4;
   wherein said carbonic anhydrase is capable of maintaining at least 50% residual activity after 15 minutes at temperatures at or above 80° C.; and
   wherein treating said carbon dioxide-containing medium is performed at temperatures between 55° C. and 120° C.

2. The method of claim 1, wherein said carbonic anhydrase is a polypeptide having at least 97% sequence identity to amino acid residues 20 to 243 of the amino acid sequence of SEQ ID NO: 2 or having at least 97% sequence identity to amino acid residues 29 to 251 of the amino acid sequence of SEQ ID NO: 4.

3. The method of claim 1, wherein said carbonic anhydrase is a polypeptide having at least 98% sequence identity to amino acid residues 20 to 243 of the amino acid sequence of SEQ ID NO: 2 or having at least 98% sequence identity to amino acid residues 29 to 251 of the amino acid sequence of SEQ ID NO: 4.

4. The method of claim 1, wherein said carbonic anhydrase is a polypeptide having at least 99% sequence identity to amino acid residues 20 to 243 of the amino acid sequence of SEQ ID NO: 2 or having at least 99% sequence identity to amino acid residues 29 to 251 of the amino acid sequence of SEQ ID NO: 4.

5. The method of claim 1, wherein said carbonic anhydrase comprises amino acid residues 20 to 243 of the amino acid sequence of SEQ ID NO: 2 or comprises amino acid residues 29 to 251 of the amino acid sequence of SEQ ID NO: 4.

6. The method of claim 1, wherein said carbon dioxide-containing medium is a gas or a multiphase mixture.

7. The method of claim 6, wherein said carbon dioxide-containing gas or multiphase mixture is emitted from combustion.

8. The method of claim 6, wherein gas as is a flue gas.

9. The method of claim 6, wherein said carbon dioxide-containing gas or multiphase mixture is a raw natural gas or a syngas.

10. The method of claim 6, wherein said carbon dioxide-containing gas or multiphase mixture is a biogas.

11. The method of claim 1, wherein said carbon dioxide-containing medium is a bicarbonate-containing liquid and said treating said carbon dioxide-containing medium is the conversion of bicarbonate to carbon dioxide.

12. The method of claim 1, wherein said carbon dioxide-containing medium further comprises an amine-based compound.

13. The method of claim 12, wherein said amine-based compound is Tris or MDEA.

14. The method of claim 11, wherein said carbon dioxide-containing medium further comprises $HPO_4^{2-}$.

15. The method of claim 1, wherein said treating said carbon dioxide-containing medium is performed at temperatures between 60° C. and 80° C.

16. The method of claim 1, wherein said treating said carbon dioxide-containing medium is performed at temperatures between 65° C. and 75° C.

17. The method of claim 1, wherein said carbonic anhydrase is capable of maintaining at least 50% residual activity after 15 minutes at temperatures at or above 90° C.

18. The method of claim 1, wherein said carbonic anhydrase is capable of maintaining at least 30% residual activity after 15 minutes at temperatures at or above 100° C.

* * * * *

SEQUENCE LISTING

```
<160> NUMBER OF SEQ ID NOS: 5

<210> SEQ ID NO 1
<211> LENGTH: 732
<212> TYPE: DNA
<213> ORGANISM: Persephonella marina

<400> SEQUENCE: 1
atgaaaaaat  ttgtagtcgg  gctttcatct  cttgtacttg  caacatcttc  atttgcaggt    60
ggtggctgga  gttatcacgg  ggaacacgga  ccggaacatt  ggggcgatct  aaaagatgaa   120
tacataatgt  gtaagatcgg  taaaaatcag  tctccggtag  atataaacag  aatagttgat   180
gcgaaattaa  aacctataaa  gatagaatac  agagcaggtg  caacaaaggt  attaaataat   240
ggacacacaa  taaaagtttc  ttacgaaccg  ggaagttata  tagttgttga  tgggataaaa   300
tttgagctga  agcagtttca  tttccacgca  ccaagtgagc  ataaattaaa  aggacagcat   360
tacccgtttg  aggctcattt  tgttcatgca  gataagcatg  gtaaccttgc  tgttataggt   420
gttttcttta  aagaaggaag  agaaaatcct  atcttagaaa  agatatggaa  agttatgcct   480
gaaaatgcag  gcgaagaggt  taaacttgca  cacaagataa  atgctgaaga  tttactgcca   540
aaggatagag  attactacag  atacagcggt  tctttaacta  ctccaccatg  ttctgaaggt   600
gtaagatgga  tagttatgga  agaggagatg  gagatgtcaa  aggagcagat  tgagaagttc   660
agaaagatta  tgggtggaga  tacaaacaga  ccggttcagc  ctttaaatgc  aagaatgatt   720
atggaaaaat  ag                                                          732

<210> SEQ ID NO 2
<211> LENGTH: 243
<212> TYPE: PRT
<213> ORGANISM: Persephonella marina

<400> SEQUENCE: 2

Met Lys Lys Phe Val Val Gly Leu Ser Ser Leu Val Leu Ala Thr Ser
 1               5                  10                  15

Ser Phe Ala Gly Gly Gly Trp Ser Tyr His Gly Glu His Gly Pro Glu
            20                  25                  30

His Trp Gly Asp Leu Lys Asp Glu Tyr Ile Met Cys Lys Ile Gly Lys
        35                  40                  45

Asn Gln Ser Pro Val Asp Ile Asn Arg Ile Val Asp Ala Lys Leu Lys
    50                  55                  60

Pro Ile Lys Ile Glu Tyr Arg Ala Gly Ala Thr Lys Val Leu Asn Asn
65                  70                  75                  80
```

Gly His Thr Ile Lys Val Ser Tyr Glu Pro Gly Ser Tyr Ile Val Val
            85                  90                  95

Asp Gly Ile Lys Phe Glu Leu Lys Gln Phe His Phe His Ala Pro Ser
            100                 105                 110

Glu His Lys Leu Lys Gly Gln His Tyr Pro Phe Glu Ala His Phe Val
            115                 120                 125

His Ala Asp Lys His Gly Asn Leu Ala Val Ile Gly Val Phe Phe Lys
            130                 135                 140

Glu Gly Arg Glu Asn Pro Ile Leu Glu Lys Ile Trp Lys Val Met Pro
145                 150                 155                 160

Glu Asn Ala Gly Glu Glu Val Lys Leu Ala His Lys Ile Asn Ala Glu
            165                 170                 175

Asp Leu Leu Pro Lys Asp Arg Asp Tyr Tyr Arg Tyr Ser Gly Ser Leu
            180                 185                 190

Thr Thr Pro Pro Cys Ser Glu Gly Val Arg Trp Ile Val Met Glu Glu
            195                 200                 205

Glu Met Glu Met Ser Lys Glu Gln Ile Glu Lys Phe Arg Lys Ile Met
            210                 215                 220

Gly Gly Asp Thr Asn Arg Pro Val Gln Pro Leu Asn Ala Arg Met Ile
225                 230                 235                 240

Met Glu Lys

<210> SEQ ID NO 3
<211> LENGTH: 756
<212> TYPE: DNA
<213> ORGANISM: Artificial Sequence
<220> FEATURE:
<223> OTHER INFORMATION: synthetic CA gene

<400> SEQUENCE: 3

```
atgaaacaac aaaaacggct ttacgcccga ttgctgacgc tgttatttgc gctcatcttc      60
ttgctgcctc attctgcagc agcggcgggc tggtcttatc acggcgagca tggccctgag     120
cattggggtg accttaaaga cgagtacatc atgtgcaaga tcggcaagaa ccaatctcct     180
gttgacatca accgcatcgt tgacgctaaa cttaaaccta tcaaaatcga gtatcgcgca     240
ggcgctacta aggttcttaa caacggccac acaatcaagg tatcttacga gcctggctct     300
tacatcgtag tagacggcat caaattcgag cttaaacaat ccatttttca tgcgccttct     360
gagcacaaac ttaaaggcca aacactatcct tttgaggctc acttcgttca tgcagacaag     420
catggcaacc ttgctgttat cggcgttttc ttcaaagaag gtcgcgagaa cccaatcctt     480
gagaagatct ggaaagtaat gcctgagaac gctggcgaag aggttaaact tgcgcacaaa     540
atcaacgctg aggaccttct tcctaaggac cgcgactact accgctactc aggctctctt     600
actactcctc cttgttctga gggcgtacgc tggatcgtaa tggaagagga gatggagatg     660
tcaaaggagc agatcgagaa attccgcaaa atcatgggtg cgacactaa tcgccctgtt     720
caacctctta acgctcgcat gatcatggag aaataa                              756
```

<210> SEQ ID NO 4
<211> LENGTH: 251
<212> TYPE: PRT
<213> ORGANISM: Artificial Sequence
<220> FEATURE:
<223> OTHER INFORMATION: Persephonella marina CA with B. licheniformis
     alpha-amylase signal peptide

<400> SEQUENCE: 4

```
Met Lys Gln Gln Lys Arg Leu Tyr Ala Arg Leu Leu Thr Leu Leu Phe
1               5                   10                  15

Ala Leu Ile Phe Leu Leu Pro His Ser Ala Ala Ala Gly Trp Ser
            20                  25                  30

Tyr His Gly Glu His Gly Pro Glu His Trp Gly Asp Leu Lys Asp Glu
        35                  40                  45

Tyr Ile Met Cys Lys Ile Gly Lys Asn Gln Ser Pro Val Asp Ile Asn
    50                  55                  60

Arg Ile Val Asp Ala Lys Leu Lys Pro Ile Lys Ile Glu Tyr Arg Ala
65                  70                  75                  80

Gly Ala Thr Lys Val Leu Asn Asn Gly His Thr Ile Lys Val Ser Tyr
            85                  90                  95

Glu Pro Gly Ser Tyr Ile Val Val Asp Gly Ile Lys Phe Glu Leu Lys
            100                 105                 110

Gln Phe His Phe His Ala Pro Ser Glu His Lys Leu Lys Gly Gln His
            115                 120                 125

Tyr Pro Phe Glu Ala His Phe Val His Ala Asp Lys His Gly Asn Leu
    130                 135                 140

Ala Val Ile Gly Val Phe Phe Lys Glu Gly Arg Glu Asn Pro Ile Leu
145                 150                 155                 160

Glu Lys Ile Trp Lys Val Met Pro Glu Asn Ala Gly Glu Glu Val Lys
            165                 170                 175

Leu Ala His Lys Ile Asn Ala Glu Asp Leu Leu Pro Lys Asp Arg Asp
            180                 185                 190

Tyr Tyr Arg Tyr Ser Gly Ser Leu Thr Thr Pro Pro Cys Ser Glu Gly
            195                 200                 205

Val Arg Trp Ile Val Met Glu Glu Glu Met Glu Met Ser Lys Glu Gln
            210                 215                 220

Ile Glu Lys Phe Arg Lys Ile Met Gly Gly Asp Thr Asn Arg Pro Val
225                 230                 235                 240

Gln Pro Leu Asn Ala Arg Met Ile Met Glu Lys
                245                 250

<210> SEQ ID NO 5
<211> LENGTH: 87
<212> TYPE: DNA
<213> ORGANISM: Bacillus Licheniformis

<400> SEQUENCE: 5
atgaaacaac aaaaacggct ttacgcccga ttgctgacgc tgttatttgc gctcatcttc      60
ttgctgcctc attctgcagc agcggcg                                          87
```